United States Patent
Wang et al.

(10) Patent No.: US 12,412,364 B2
(45) Date of Patent: Sep. 9, 2025

(54) SYSTEMS AND METHODS FOR OBJECT RECOGNITION

(71) Applicant: SHANGHAI UNITED IMAGING HEALTHCARE CO., LTD., Shanghai (CN)

(72) Inventors: Xiaodong Wang, Shanghai (CN); Xiong Yang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 379 days.

(21) Appl. No.: 18/049,283

(22) Filed: Oct. 24, 2022

(65) Prior Publication Data

US 2023/0074296 A1 Mar. 9, 2023

Related U.S. Application Data

(63) Continuation of application No. PCT/CN2020/137816, filed on Dec. 19, 2020.

(30) Foreign Application Priority Data

Apr. 24, 2020 (CN) .......................... 202010333819.5
Jun. 9, 2020 (CN) .......................... 202010518681.6

(51) Int. Cl.
 *G06V 10/44* (2022.01)
 *G06V 10/75* (2022.01)
 (Continued)

(52) U.S. Cl.
 CPC ............ *G06V 10/454* (2022.01); *G06V 10/44* (2022.01); *G06V 10/757* (2022.01); *G06V 10/82* (2022.01);
 (Continued)

(58) Field of Classification Search
 CPC ...... G06V 10/454; G06V 40/14; G06V 10/82; G06V 10/44; G06V 10/757;
 (Continued)

(56) References Cited

U.S. PATENT DOCUMENTS 9,767,557 B1 * 9/2017 Gulsun ............ G06V 30/19173
9,788,729 B2 10/2017 Waku et al.
(Continued)

FOREIGN PATENT DOCUMENTS

CN 103247073 8/2013
CN 106548213 A 3/2017
(Continued)

OTHER PUBLICATIONS

Wei Wu, et al, "CAR-Net: A deep Learning-Based Deformation Model for 3D/2D Coronary Artery Registration", IEEE (Year: 2022).*

(Continued)

*Primary Examiner* — Aaron W Carter
*Assistant Examiner* — Alejandro Hernandez
(74) *Attorney, Agent, or Firm* — Metis IP LLC

(57) ABSTRACT

The present disclosure relates to systems and methods for object recognition. The systems may obtain image data captured by an imaging device. The image data may include one or more objects. The systems may determine a centerline of a target object in the one or more objects based on the image data. The systems may determine a recognition result of the target object using a trained neural network model based on at least one feature parameter of the centerline of the target object. The recognition result may include a name of the target object. The systems may perform an anomaly detection on the target object based on the recognition result of the target object.

19 Claims, 17 Drawing Sheets

(51) Int. Cl.
*G06V 10/82* (2022.01)
*G06V 40/14* (2022.01)

(52) U.S. Cl.
CPC ........ *G06V 40/14* (2022.01); *G06V 2201/031* (2022.01)

(58) Field of Classification Search
CPC ............. G06V 2201/031; G06V 20/64; G06V 10/25; G06V 10/22; G06T 7/0012; G06T 7/11; G06T 7/0002; G06T 11/003; G06T 7/60; G06T 7/33; G06T 7/10; A61B 5/055; A61B 5/02007; A61B 5/02; A61B 6/03; A61B 6/5217; A61B 6/5211; A61B 6/52; G06N 3/02; G16B 45/00; G16H 30/40; G16H 30/20; G06K 9/62; G06K 9/6228
See application file for complete search history.

(56) References Cited

U.S. PATENT DOCUMENTS

| | | | |
|---|---|---|---|
| 10,258,304 B1* | 4/2019 | Kiraly | A61B 5/08 |
| 11,100,685 B2* | 8/2021 | Liang | G16H 50/20 |
| 11,116,575 B2* | 9/2021 | Taylor | A61M 5/007 |
| 11,147,635 B1* | 10/2021 | Sganga | A61B 34/20 |
| 2002/0086347 A1 | 7/2002 | Johnson et al. | |
| 2005/0105786 A1 | 5/2005 | Moreau-Gobard et al. | |
| 2007/0265550 A1 | 11/2007 | Choi et al. | |
| 2010/0046815 A1 | 2/2010 | Von Berg et al. | |
| 2010/0076296 A1 | 3/2010 | Mittal et al. | |
| 2010/0128963 A1 | 5/2010 | Waku et al. | |
| 2010/0135561 A1* | 6/2010 | Moulik | G06T 7/0012 382/131 |
| 2011/0224542 A1 | 9/2011 | Mittal et al. | |
| 2011/0235891 A1 | 9/2011 | Sonnemans et al. | |
| 2014/0094691 A1 | 4/2014 | Steinberg et al. | |
| 2017/0262733 A1* | 9/2017 | Gulsun | G06V 10/454 |
| 2017/0277977 A1* | 9/2017 | Kitamura | G06T 7/0012 |
| 2017/0372475 A1 | 12/2017 | Gulsun et al. | |
| 2018/0068437 A1 | 3/2018 | Bronkalla et al. | |
| 2019/0029625 A1 | 1/2019 | Zhong et al. | |
| 2019/0130578 A1 | 5/2019 | Gulsun et al. | |
| 2019/0180153 A1* | 6/2019 | Buckler | G06F 18/29 |
| 2019/0318476 A1* | 10/2019 | Isgum | A61B 6/507 |
| 2019/0325579 A1 | 10/2019 | Wang et al. | |
| 2019/0362855 A1* | 11/2019 | Ma | G06T 7/0016 |
| 2020/0069197 A1 | 3/2020 | Samarage et al. | |
| 2020/0113450 A1* | 4/2020 | Nishioka | A61B 5/743 |
| 2020/0402666 A1* | 12/2020 | Wang | G06N 3/084 |
| 2021/0158533 A1 | 5/2021 | Cui et al. | |
| 2021/0241484 A1* | 8/2021 | Wang | A61B 5/0022 |
| 2021/0374950 A1* | 12/2021 | Gao | G06T 7/70 |
| 2022/0004797 A1* | 1/2022 | Kitamura | G06V 10/25 |
| 2022/0139529 A1 | 5/2022 | Bhatia et al. | |
| 2022/0215956 A1* | 7/2022 | Kong | G06T 7/0012 |
| 2023/0074296 A1* | 3/2023 | Wang | G06T 7/0012 |
| 2023/0394654 A1* | 12/2023 | Hampe | A61B 6/504 |
| 2024/0023937 A1* | 1/2024 | Wong | A61B 8/5223 |
| 2024/0037952 A1* | 2/2024 | Matsumoto | G06V 10/255 |
| 2024/0386547 A1* | 11/2024 | Nadakuditi | G06T 7/0012 |

FOREIGN PATENT DOCUMENTS

| | | | |
|---|---|---|---|
| CN | 107273657 | | 10/2017 |
| CN | 107563983 A | | 1/2018 |
| CN | 107644420 | | 1/2018 |
| CN | 108765385 | | 11/2018 |
| CN | 110163928 | | 8/2019 |
| CN | 110390282 A | * | 10/2019 |
| CN | 110570929 | | 12/2019 |
| CN | 110675481 A | | 1/2020 |
| CN | 110889896 A | | 3/2020 |
| CN | 111145173 | | 5/2020 |
| CN | 111461065 A | | 7/2020 |
| CN | 111681224 A | | 9/2020 |
| CN | 111681226 A | | 9/2020 |
| CN | 108717695 B | | 7/2021 |
| CN | 109544543 B | | 8/2021 |
| CN | 116912081 A | * | 10/2023 |
| WO | WO-2019005722 A1 | * | 1/2019 ......... G06F 18/2413 |

OTHER PUBLICATIONS

International Search Report in PCT/CN2020/137816 mailed on Mar. 18, 2021, 5 pages.
Written Opinion in PCT/CN2020/137816 mailed on Mar. 18, 2021, 5 pages.
International Search Report in PCT/CN2021/099197 mailed on Sep. 8, 2021, 4 pages.
Written Opinion in PCT/CN2021/099197 mailed on Sep. 8, 2021, 6 pages.
The Extended European Search Report in European Application No. 20932198.3 mailed on Aug. 11, 2023, 8 pages.
Cheng, Shiyin et al., Centerline extraction from MR carotid angiography images, Chinese Journal of Stereology and Image Analysis, 21(4): 415-422, 2016.
Kirisli et al., Standardized evaluation framework for evaluating coronary artery stenosis detection, stenosis quantification and lumen segmentation algorithms in computed tomography angiography, Medical Image Analysis, 17: 859-876, 2013.

* cited by examiner

SYSTEMS AND METHODS FOR OBJECT RECOGNITION

CROSS-REFERENCE TO RELATED APPLICATIONS

This application is a Continuation of International Application No. PCT/CN2020/137816, filed on Dec. 19, 2020, which claims priority to Chinese Patent Application No. 202010333819.5 filed on Apr. 24, 2020 and Chinese Patent Application No. 202010518681.6 filed on Jun. 9, 2020, the contents of each of which are incorporated herein by reference in their entirety.

TECHNICAL FIELD

The present disclosure generally relates to image processing technology, and more particularly, relates to systems and methods for recognizing a tubular structure.

BACKGROUND

In the process of disease diagnosis and/or treatment for various medical conditions (e.g., tumors, coronary heart diseases, or brain diseases), a doctor needs to analyze tubular structures (e.g., blood vessels, the trachea, nerves, etc.) of a subject (e.g., a patient). Generally, in order to view the tubular structures, the doctor may manually look through each two-dimensional layer in a three-dimensional image of the subject obtained by medical imaging (e.g., computed tomography (CT), magnetic resonance imaging (MRI)), which has low efficiency and accuracy. In addition, in some situations, in order to analyze a tubular structure more accurately, the doctor needs to view the full appearance of the tubular structure. Therefore, it is desirable to provide systems and methods for recognizing the tubular structure with improved efficiency and accuracy.

SUMMARY

An aspect of the present disclosure relates to a system for object recognition. The system may include at least one storage medium including a set of instructions and at least one processor in communication with the at least one storage medium. When executing the set of instructions, the at least one processor may be directed to cause the system to implement operations. The operations may include obtaining image data captured by an imaging device. The image data may include one or more objects. The operations may include determining a centerline of a target object in the one or more objects based on the image data. The operations may include determining a recognition result of the target object using a trained neural network model based on at least one feature parameter of the centerline of the target object. The recognition result may include a name of the target object.

In some embodiments, the target object may include a tubular structure.

In some embodiments, the determining, based on at least one feature parameter of the centerline of the target object, a recognition result of the target object using a trained neural network model may include determining a reference centerline of at least one reference object associated with the target object among the one or more objects based on the image data, the centerline of the target object and the reference centerline of the at least one reference object forming a centerline tree; determining at least one feature parameter of the centerline tree; and determining, based on the at least one feature parameter of the centerline of the target object and the at least one feature parameter of the centerline tree, the recognition result of the target object using the trained neural network model.

In some embodiments, the at least one feature parameter of the centerline of the target object may include position information of the centerline in the image data, position information of the centerline in the centerline tree, information of the centerline tree, and/or size information of the centerline.

In some embodiments, the trained neural network model may include a first recognition module, an extraction module, and a second recognition module. The first recognition module may be configured to determine a preliminary recognition result of the target object based on the at least one feature parameter of the centerline. The extraction module may be configured to determine the at least one feature parameter of the centerline tree based on the centerline tree. The second recognition module may be configured to determine the recognition result of the target object based on the preliminary recognition result and the at least one feature parameter of the centerline tree.

In some embodiments, the target object may include a plurality of portions. To determine a preliminary recognition result of the target object based on the at least one feature parameter of the centerline, the first recognition module may be further configured to determine the preliminary recognition result of the target object based on at least one feature parameter of a portion of the centerline corresponding to each of at least one of the plurality of portions in the target object.

In some embodiments, the extraction module may include a recurrent neural network model. The recurrent neural network model may include a plurality of nodes. To determine the at least one feature parameter of the centerline tree based on the centerline tree, the extraction module may be further configured to determine the at least one feature parameter of the centerline tree by inputting at least one feature parameter of each centerline in the centerline tree into one of the plurality of nodes corresponding to the centerline in the centerline tree.

In some embodiments, the trained neural network model may be obtained by a training process. The training process may include obtaining a plurality of training samples associated with a plurality of sample objects. Each of the plurality of training samples may include at least one feature parameter of a centerline of a sample object associated with the training sample and a name of the sample object. The training process may further include obtaining the trained neural network model by iteratively training a preliminary neural network model based on the plurality of training samples. In each iteration, at least one feature parameter of a centerline of a sample object may be used as an input of the preliminary neural network model, the name of the sample object may be used as a reference output of the preliminary neural network model, values of model parameters of the preliminary neural network model may be updated by comparing the reference output and an estimated output of the preliminary neural network model generated based on the input of the preliminary neural network model.

In some embodiments, the trained neural network model may include a recurrent neural network (RNN) or a long short-term memory (LSTM) neural network.

In some embodiments, each of the plurality of training samples may include at least one feature parameter of a centerline tree corresponding to a sample object associated with the training sample. The obtaining a plurality of training samples associated with a plurality of sample objects may include extracting a centerline of each sample object in a sample image; labeling the centerline of the sample object as an anatomical name of the sample object; and determining a centerline tree associated with the sample object based on the centerline of the sample object. The centerline tree associated with the sample object may include the centerline of the sample object and a reference centerline of at least one reference object associated with the sample object.

In some embodiments, the target object may include a plurality of portions. The recognition result of the target object may include a name of each of the plurality of portions.

In some embodiments, the operations may further include determining whether the target object includes an abnormality and determining, in response to determining that the target object includes the abnormality, location information of the abnormality based on the recognition result of the target object.

In some embodiments, the determining whether the target object includes an abnormality may include obtaining a plurality of image slices of the target object, each of the plurality of image slices representing a layer of the target object in a direction perpendicular to the centerline of the target object; for each of the plurality of image slices, obtaining at least one feature parameter of the target object from the image slice; and determining whether the target object includes the abnormality based on the at least one feature parameter of the target object obtained from the image slice.

In some embodiments, the target object may include a tubular structure. The at least one feature parameter of the target object may include at least one structural parameter of a lumen or a tube wall of the tubular structure. The determining whether the target object includes the abnormality based on the at least one feature parameter of the target object obtained from the image slice may include performing a tube diameter analysis on the tubular structure based on the at least one structural parameter of the lumen or the tube wall of the tubular structure and determining whether the target object includes the abnormality based on the tube diameter analysis result.

In some embodiments, the image data may include a plurality of image slices representing a same position of the subject. Each of the plurality of image slices may be acquired by the imaging device according to one of a plurality of registration sequences.

A further aspect of the present disclosure relates to a method for object recognition. The method may be implemented on a computing device including at least one processor, at least one storage medium, and a communication platform connected to a network. The method may include obtaining image data captured by an imaging device. The image data may include one or more objects. The method may include determining a centerline of a target object in the one or more objects based on the image data. The method may include determining a recognition result of the target object using a trained neural network model based on at least one feature parameter of the centerline of the target object. The recognition result may include a name of the target object.

A still further aspect of the present disclosure relates to a system for object recognition. The system may include an obtaining module, a centerline determination module, and a recognition module. The obtaining module may be configured to obtain image data captured by an imaging device. The image data may include one or more objects. The centerline determination module may be configured to determine a centerline of a target object in the one or more objects based on the image data. The recognition module may be configured to determine a recognition result of the target object using a trained neural network model based on at least one feature parameter of the centerline of the target object. The recognition result may include a name of the target object.

A still further aspect of the present disclosure relates to a non-transitory computer readable medium including executable instructions. When the executable instructions are executed by at least one processor, the executable instructions may direct the at least one processor to perform a method. The method may include obtaining image data captured by an imaging device. The image data may include one or more objects. The method may include determining a centerline of a target object in the one or more objects based on the image data. The method may include determining a recognition result of the target object using a trained neural network model based on at least one feature parameter of the centerline of the target object. The recognition result may include a name of the target object.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
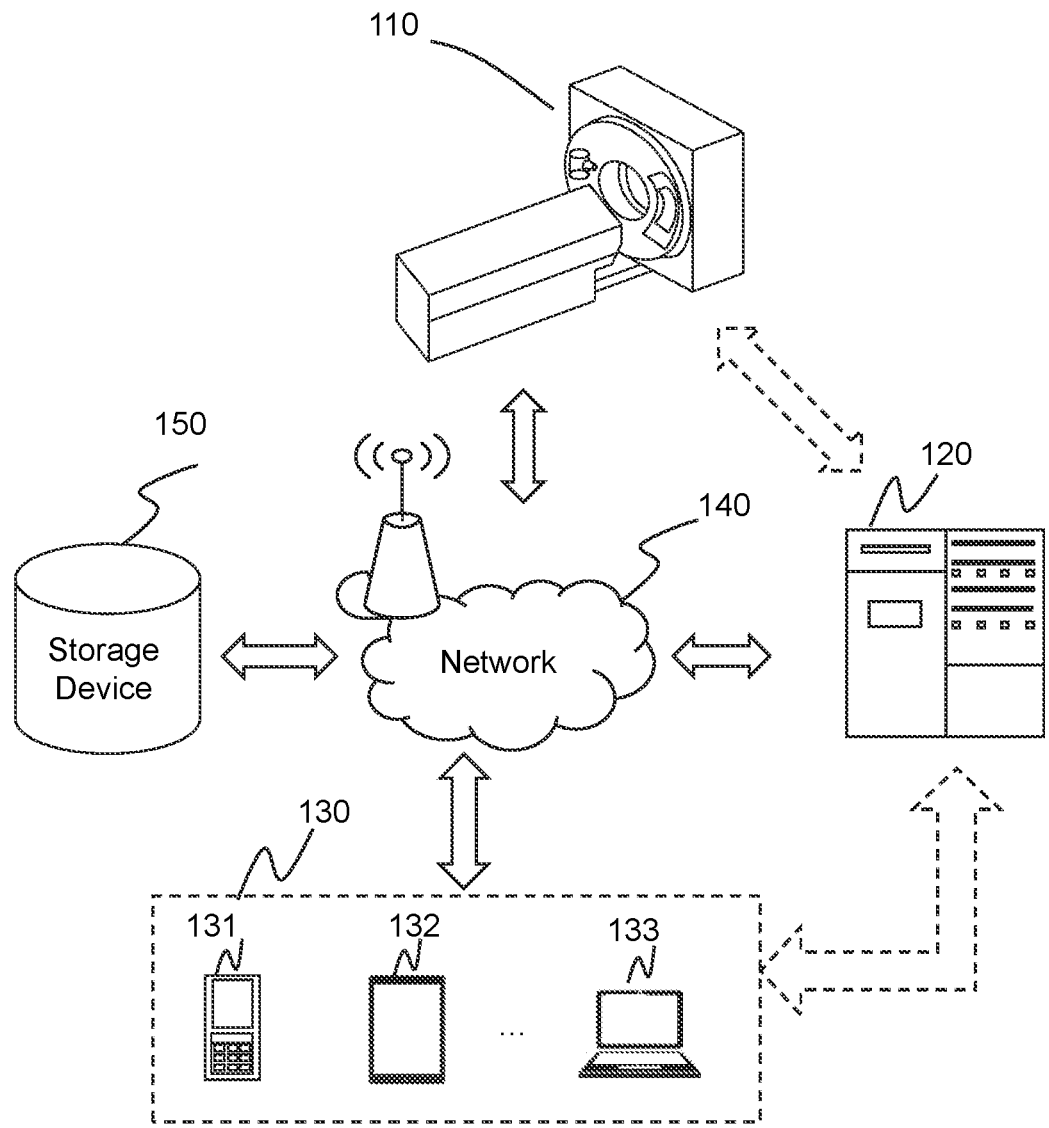
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the terms "system," "unit," "module," and/or "block" used herein are one method to distinguish different components, elements, parts, sections, or assemblies of different levels in ascending order. However, the terms may be displaced by another expression if they achieve the same purpose.

Generally, the words "module," "unit," or "block," as used herein, refer to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 illustrated in FIG. 2 and/or the central processing unit (CPU) 340 illustrated FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

An aspect of the present disclosure relates to systems and methods for object recognition. The systems may obtain an image (e.g., a computed tomography (CT) image, a magnetic resonance (MR) image) captured by an imaging device. The image may include one or more objects, for example, a tubular structure (e.g., blood vessels, trachea, nerves, large intestine, small intestine, etc.). The systems may determine a centerline of a target object (e.g., each of the one or more objects) in the one or more objects based on the image. According to at least one feature parameter of the centerline, the systems may determine a recognition result of the target object using a trained neural network model (e.g., a recurrent neural network (RNN), a long short-term memory (LSTM) neural network). The recognition result may include a name of the target object. Further, the systems may determine whether the target object includes an abnormality (e.g., a lesion). In response to determining that the target object includes the abnormality, the systems may determine location information of the abnormality based on the recognition result of the target object.

According to the systems and methods of the present disclosure, the target object in the image may be automatically and efficiently recognized via the trained neural network model. According to the recognition result of the target object, a doctor may select and view the full appearance of the target object. Further, the target object may be automatically analyzed instead of the doctor's manual analysis of the target object. For example, whether the target object includes an abnormality may be determined, and then the location information of the abnormality may be determined based on the recognition result of the target object when the target object includes the abnormality, which may improve the efficiency and accuracy of the analysis of target object.

FIG. 1 is a schematic diagram illustrating an exemplary medical system according to some embodiments of the present disclosure. As illustrated, the medical system 100 may include an imaging device 110, a processing device 120, a terminal device 130, a network 140, and a storage device 150. The components of the medical system 100 may be connected in one or more of various ways. Mere by way of example, as illustrated in FIG. 1, the imaging device 110 may be connected to the processing device 120 through the network 140. As another example, the imaging device 110 may be connected to the processing device 120 directly (as indicated by the bi-directional arrow in dotted lines linking the imaging device 110 and the processing device 120). As a further example, the storage device 150 may be connected to the processing device 120 directly or through the network 140. As still a further example, the terminal device 130 may be connected to the processing device 120 directly (as indicated by the bi-directional arrow in dotted lines linking the terminal device 130 and the processing device 120) or through the network 140.

The imaging device 110 may be configured to acquire image data relating to at least one part of a subject. The imaging device 110 may scan the subject or a portion thereof that is located within its detection region and generate image data relating to the subject or the portion thereof. The image data relating to at least one part of a subject may include one or more images, projection data, or a combination thereof. In some embodiments, the image data may be two-dimensional (2D) image data, three-dimensional (3D) image data, four-dimensional (4D) image data, or the like, or any combination thereof. In some embodiments, the imaging device 110 may include a single modality imaging device. For example, the imaging device 110 may include a digital subtraction angiography (DSA), a positron emission tomography (PET) device, a single-photon emission computed tomography (SPECT) device, a magnetic resonance imaging (MRI) device (also referred to as an MR device, an MR scanner), a computed tomography (CT) device, an ultrasonography scanner, a digital radiography (DR) scanner, or the like, or any combination thereof. In some embodiments, the imaging device 110 may include a multi-modality imaging device. Exemplary multi-modality imaging devices may include a PET-CT device, a PET-MR device, or the like, or a combination thereof.

The processing device 120 may process data and/or information obtained from the imaging device 110, the terminal device 130, and/or the storage device 150. For example, the processing device 120 may obtain one or more images captured by the imaging device 110. Further, the processing device 120 may determine a centerline of a target object in the one or more objects based on the images. According to at least one feature parameter of the centerline, the processing device 120 may determine a recognition result of the target object using a trained neural network model. In some embodiments, the processing device 120 may include a central processing unit (CPU), a digital signal processor (DSP), a system on a chip (SoC), a microcontroller unit (MCU), or the like, or any combination thereof. In some embodiments, the processing device 120 may include a computer, a user console, a single server or a server group, etc. The server group may be centralized or distributed. In some embodiments, the processing device 120 may be local or remote. For example, the processing device 120 may access information and/or data stored in the imaging device 110, the terminal device 130, and/or the storage device 150 via the network 140. As another example, the processing device 120 may be directly connected to the imaging device 110, the terminal device 130, and/or the storage device 150 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 or a portion of the processing device 120 may be integrated into the imaging device 110. In some embodiments, the processing device 120 may be implemented by a computing device 200 including one or more components as described in FIG. 2.

The terminal device 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the smart mobile device may include a mobile phone, a personal digital assistant (PDA), a gaming device, a navigation device, a point of sale (POS) device, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal device 130 may be part of the processing device 120.

The network 140 may include any suitable network that can facilitate the exchange of information and/or data for the medical system 100. In some embodiments, one or more components (e.g., the imaging device 110, the processing device 120, the storage device 150, the terminal device 130) of the medical system 100 may communicate information and/or data with one or more other components of the medical system 100 via the network 140. For example, the processing device 120 may obtain data from the imaging device 110 via the network 140. As another example, the terminal device 130 may receive the recognition result of the target object from the processing device 120 via the network 140. A user may select one of multiple target objects based on recognition results of the multiple target objects via the terminal device 130 and the processing device 120 may analyze the selected target object. In some embodiments, one or more components (e.g., the imaging device 110, the processing device 120, the storage device 150, the terminal device 130) of the medical system 100 may communicate information and/or data with one or more external resources such as an external database of a third party, etc. For example, the processing device 120 may obtain a trained neural network model from a database of a vendor or manufacture (e.g., a manufacture of the imaging device 110) that provides and/or updates the trained neural network model. The network 140 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 140 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 140 may include one or more network access points. For example, the network 140 may include wired and/or wireless network access points, such as base stations and/or internet exchange points, through which one or more components of the medical system 100 may be connected to the network 140 to exchange data and/or information.

The storage device 150 may store data, instructions, and/or any other information. In some embodiments, the storage device 150 may store data obtained from the imaging device 110, the terminal device 130, and/or the processing device 120. In some embodiments, the storage device 150 may store data and/or instructions that the processing device 120 may execute or use to perform exemplary methods described in the present disclosure. In some embodiments, the storage device 150 may include a mass storage device, a removable storage device, a volatile read-and-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 150 may be implemented on a cloud platform as described elsewhere in the disclosure.

In some embodiments, the storage device 150 may be connected to the network 140 to communicate with one or more components (e.g., the imaging device 110, the processing device 120, the terminal device 130) of the medical system 100. One or more components of the medical system 100 may access the data or instructions stored in the storage device 150 via the network 140. In some embodiments, the storage device 150 may be directly connected to or communicate with one or more components of the medical system 100. In some embodiments, the storage device 150 may be part of the processing device 120 or the terminal device 130.

It should be noted that the above description of the medical system 100 is merely provided for the purposes of illustration, and not intended to limit the scope of the present disclosure. For persons having ordinary skills in the art, multiple variations and modifications may be made under the teachings of the present disclosure. For example, the medical system 100 may include one or more additional components and/or one or more components of the medical system 100 described above may be omitted. Additionally or alternatively, two or more components of the medical system 100 may be integrated into a single component. A component of the medical system 100 may be implemented on two or more sub-components.

Figure 2:
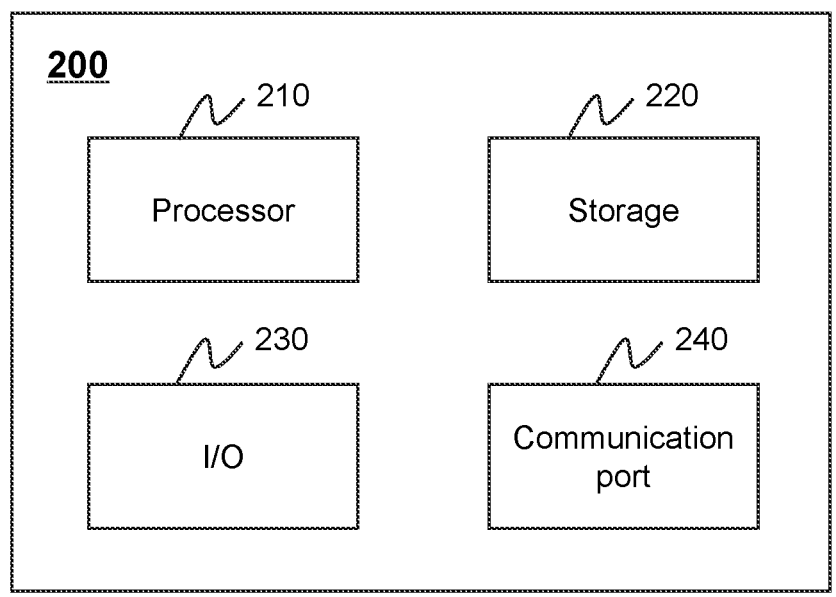
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. The computing device 200 may be used to implement any component of the medical system 100 as described herein. For example, the processing device 120 and/or the terminal device 130 may be implemented on the computing device 200, respectively, via its hardware, software program, firmware, or a combination thereof. Although only one such computing device is shown, for convenience, the computer functions relating to the medical system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program codes) and perform functions of the processing device 120 in accordance with techniques described herein. The computer instructions may include, for example, routines, programs, objects, components, data structures, procedures, modules, and functions, which perform particular functions described herein. For example, the processor 210 may process data obtained from the imaging device 110, the storage device 150, the terminal device 130, and/or any other components of the medical system 100.

In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or a combination thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the storage device 150, the terminal device 130, and/or any other component of the medical system 100. In some embodiments, the storage 220 may include a mass storage device, a removable storage device, a volatile read-and-write memory, a read-only memory (ROM), or the like, or a combination thereof. In some embodiments, the storage 220 may store one or more programs and/or instructions to perform exemplary methods described in the present disclosure. For example, the storage 220 may store a program for the processing device 120 to execute to determine a trained neural network model. As another example, the storage 220 may store a program for the processing device 120 to execute to apply the trained neural network model to determine a recognition result of the target object.

The I/O 230 may input and/or output signals, data, information, etc. In some embodiments, the I/O 230 may enable user interaction with the processing device 120. In some embodiments, the I/O 230 may include an input device and an output device. The input device may include alphanumeric and other keys that may be input via a keyboard, a touch screen (for example, with haptics or tactile feedback), a speech input, an eye-tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 140) to facilitate data communications. The communication port 240 may establish connections between the processing device 120 and one or more components (e.g., the imaging device 110, the storage device 150, and/or the terminal device 130) of the medical system 100. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
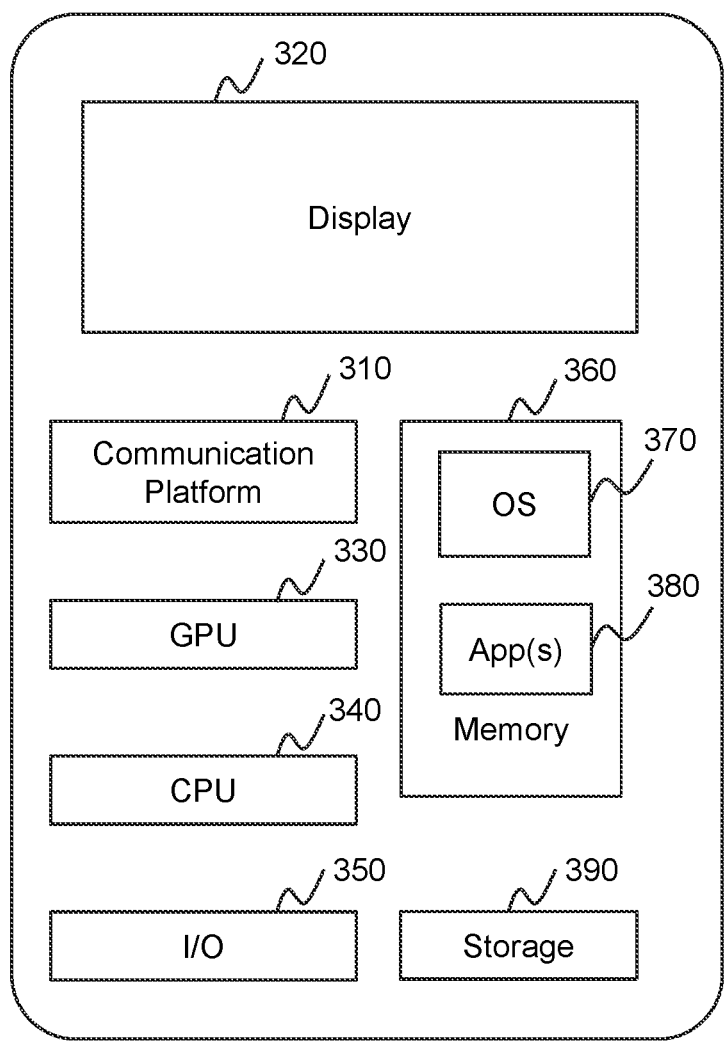
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, one or more components (e.g., the terminal device 130, the processing device 120) of the medical system 100 may be implemented on one or more components of the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to the medical system 100. User interactions with the information stream may be achieved via the I/O 350 and provided to the processing device 120 and/or other components of the medical system 100 via the network 140.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
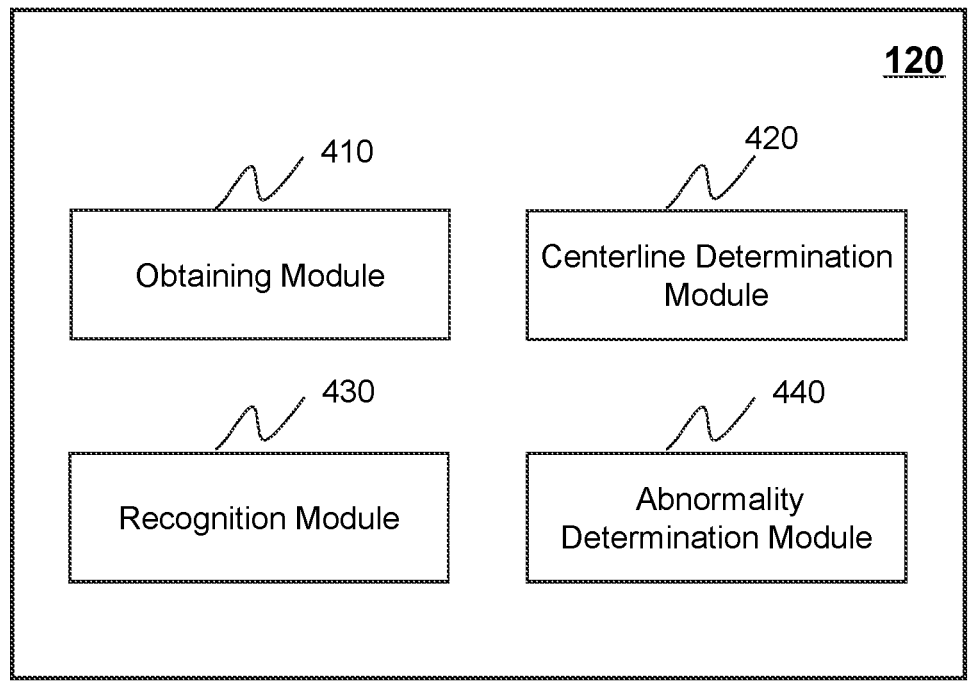
FIGS. 4A-B are block diagrams illustrating exemplary processing devices according to some embodiments of the present disclosure.
Figure 4B:
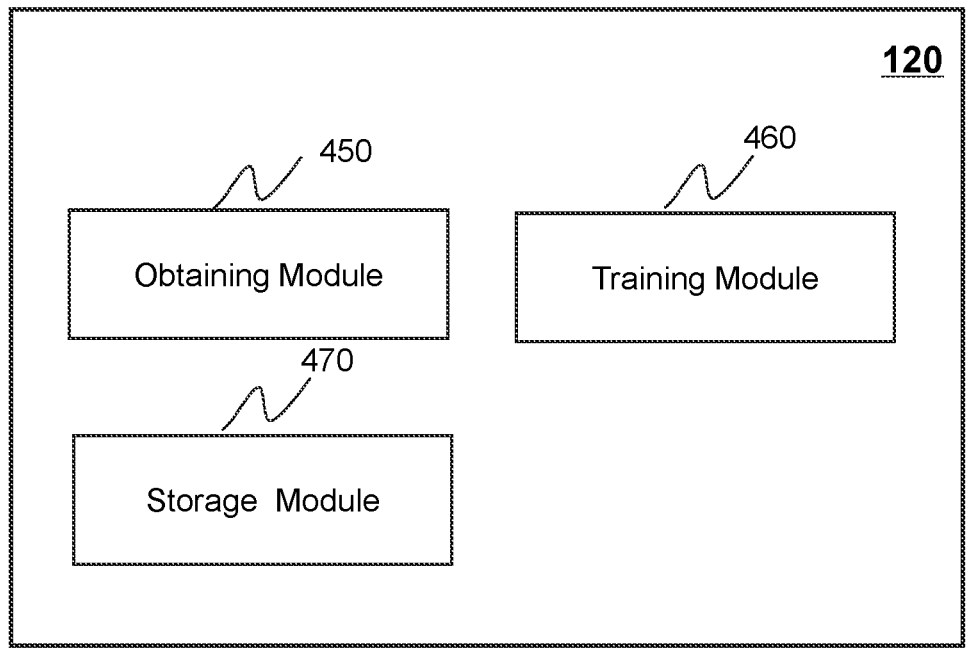

FIGS. 4A-B are block diagrams illustrating exemplary processing devices according to some embodiments of the present disclosure. The processing device 120 may be implemented on the computing device 200 (e.g., the processor 210) illustrated in FIG. 2 or the mobile device 300 illustrated in FIG. 3.

As illustrated in FIG. 4A, the processing device 120 may include an obtaining module 410, a centerline determination module 420, a recognition module 430, and an abnormality determination module 440.

The obtaining module 410 may be configured to obtain image data captured by an imaging device (e.g., the imaging device 110). More descriptions regarding the obtaining of the image data may be found elsewhere in the present disclosure, for example, operation 510 in FIG. 5 and relevant descriptions thereof.

The centerline determination module 420 may be configured to determine a centerline of a target object in the one or more objects based on the image data. More descriptions regarding the determination of the centerline of the target object may be found elsewhere in the present disclosure, for example, operation 520 in FIG. 5 and relevant descriptions thereof.

The recognition module 430 may be configured to determine a recognition result of the target object based on at least one feature parameter of the centerline of the target object using a trained neural network model. More descriptions regarding the determination of the recognition result of the target object may be found elsewhere in the present disclosure, for example, operation 530 in FIG. 5 and relevant descriptions thereof.

The abnormality determination module 440 may be configured to perform an anomaly detection on the target object based on the recognition result of the target object. More descriptions regarding the anomaly detection of the target object may be found elsewhere in the present disclosure, for example, operation 540 in FIG. 5 and relevant descriptions thereof.

As illustrated in FIG. 4B, the processing device 120 may further include an obtaining module 450, a training module 460, and a storage module 470.

The obtaining module 450 may be configured to obtain a plurality of training samples associated with a plurality of sample objects. More descriptions regarding the obtaining of the plurality of training samples may be found elsewhere in the present disclosure, for example, operation 610 in FIG. 6 and relevant descriptions thereof.

The training module 460 may be configured to obtain the trained neural network model by iteratively training a preliminary neural network model based on the plurality of training samples. More descriptions regarding the obtaining of the trained neural network model may be found elsewhere in the present disclosure, for example, operation 620 in FIG. 6 and relevant descriptions thereof.

The storage module 470 may be configured to store information and/or data (e.g., the image, the at least one feature parameter of the centerline, the trained neural network model, the recognition result of the target object) associated with the object recognition.

The modules in the processing device 120 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

It should be noted that the above description regarding the processing device 120 is merely provided for the purposes of illustration, and not intended to limit the scope of the present disclosure. For persons having ordinary skills in the art, multiple variations and modifications may be made under the teachings of the present disclosure. In some embodiments, two or more of the modules may be combined into a single module, and any one of the modules may be divided into two or more units. For example, the centerline determination module 420 and the abnormality determination module 440 may be combined as a single module which may both determine the centerline of the target object and whether the target object includes the abnormality. In some embodiments, the processing device 120 may include one or more additional modules. For example, the processing device 120 may also include a transmission module (not shown) configured to transmit signals (e.g., electrical signals, electromagnetic signals) to one or more components (e.g., the imaging device 110, the terminal device 130, the storage device 150) of the medical system 100. In some embodiments, the training module 460 may be implemented on a separate device (e.g., a processing device independent from the processing device 120). In some embodiments, the training module 460 may be unnecessary and the trained neural network model may be obtained from a storage device (e.g., the storage device 150, an external database) disclosed elsewhere in the present disclosure. However, those variations and modifications do not depart from the scope of the present disclosure.

Figure 5:
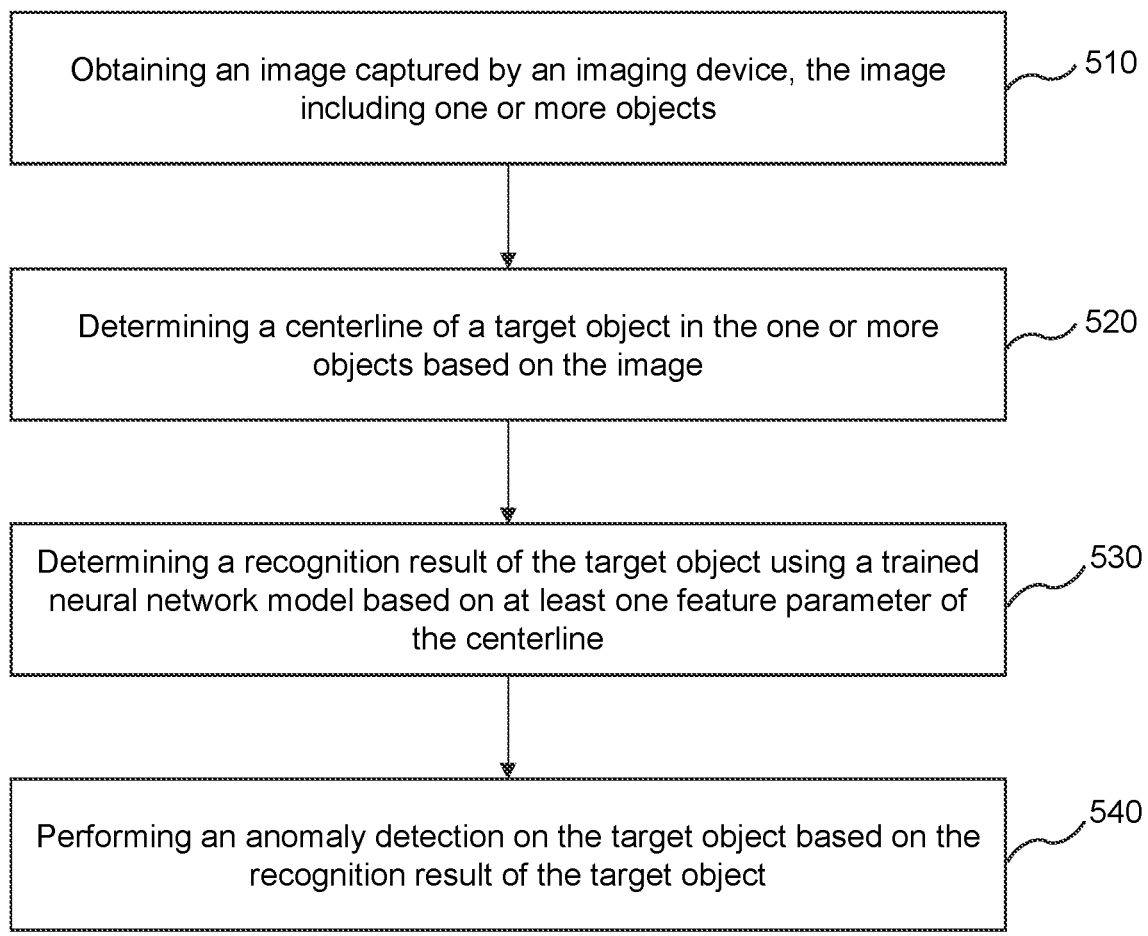
FIG. 5 is a flowchart illustrating an exemplary process for object recognition according to some embodiments of the present disclosure.

FIG. 5 is a flowchart illustrating an exemplary process for object recognition according to some embodiments of the present disclosure. In some embodiments, process 500 may be executed by the medical system 100. For example, the process 500 may be implemented as a set of instructions (e.g., an application) stored in a storage device (e.g., the storage device 150, the storage 220, and/or the storage 390). In some embodiments, the processing device 120 (e.g., the processor 210 of the computing device 200, the CPU 340 of the mobile device 300, and/or one or more modules illustrated in FIG. 4), an object recognition device 1200 (e.g., one or more units illustrated in FIG. 12), and/or a target tissue positioning device 1700 (e.g., one or more units illustrated in FIG. 17) may execute the set of instructions and may accordingly be directed to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In 510, the processing device 120 (e.g., the obtaining module 410) (e.g., the interface circuits of the processor 210) may obtain image data (e.g., an image) captured by an imaging device (e.g., the imaging device 110).

In some embodiments, the processing device 120 may direct or cause the imaging device 110 to perform a scan (e.g., an MR scan, a CT scan) on a subject and determine the image data based on scanning data obtained from the imaging device 110. For example, the processing device 120 may obtain the scanning data (e.g., k-space data) acquired by an MR scanner through executing one or more scan pulse sequences (also referred to as sequences), and reconstruct the image data based on the scanning data using an image reconstruction technique. The one or more scan pulse sequences may be the same sequence or a plurality of sequences that are different. Merely by way of example, the scan pulse sequences may include a bright blood sequence (e.g., a time of flight (Tof) scan sequence), a black blood sequence (e.g., a T1 enhanced scan sequence, a T2 enhanced scan sequence), or the like, or any combination thereof. In such cases, the image data may include one or more T1 images, one or more T2 images, one or more proton density images, etc. In some embodiments, the plurality of sequences may include a plurality of registration sequences. The image data acquired based on the plurality of sequences may include a plurality of image slices each of which represents a same position or portion of the subject acquired based on one of the plurality of sequences. The plurality of registration sequences may refer to sequences that have a registration relationship between any two of the plurality of sequences. In other words, images acquired by an MR image via scanning a same position of a subject using at least two registration sequences may satisfy the registration relationship. One of the images may be determined based on others of the images based on the registration relationship.

As used herein, the subject may include a biological subject and/or a non-biological subject. The biological subject may be a human being, an animal, a plant, or a specific portion, organ, and/or tissue thereof. For example, the subject may include the head, the neck, the thorax, the heart, the stomach, one or more blood vessels, a soft tissue, a tumor, a nodule, or the like, or any combination thereof. In some embodiments, the subject may be a man-made component of organic and/or inorganic matters that are with or without life.

In some embodiments, the image data may be previously determined and stored in a storage device (e.g., the storage device 150, the storage device 220, and/or the storage 390). The processing device 120 may obtain the image data from the storage device via a network (e.g., the network 140).

In some embodiments, the image data may include one or more two-dimensional (2D) images, a three-dimensional (3D) image of the subject, etc. Each of the one or more 2D images may correspond to a layer of the subject parallel to a certain plane. In some embodiments, the plane may include a coronal plane, a coronal plane, a transverse plane, etc. In some embodiments, the 3D image may include a plurality of two-dimensional (2D) image layers. In some embodiments, the image data may include a plurality of image layers (or slices) each of which represents the same position or portion of the subject acquired by the MR device according to one of the plurality of registration sequences.

In some embodiments, the subject may include one or more objects and the image data may include a representation of the one or more objects. The one or more objects may include tubular structures, such as blood vessels, at least a portion of the trachea, nerves, the large intestine, the small intestine, etc. In some embodiments, the one or more objects may include tubular structures with different anatomical structures. The tubular structures with different anatomical structures may have different names (also referred to as anatomical names). For example, cerebral blood vessels may include the vertebral artery, the internal carotid artery, etc. As another example, nerves may include spinal nerves, axillary nerves, radial nerves, cutaneous nerves, etc.

In some embodiments, a tubular structure may include a plurality of portions (or regions) with different anatomical structures. The portions with different anatomical structures may have different names. For example, the vertebral artery may include the outer bone segment (i.e., V1 segment), the intervertebral foramina segment (i.e., V2 segment), the outer spinal segment (i.e., V3 segment), and the intradural segment (i.e., V4 segment). As another example, the internal carotid may include the artery strong segment (i.e., C1 segment), the rock segment (i.e., C2 segment), the fractured hole segment (i.e., C3 segment), the cavernous sinus segment (i.e., C4 segment), the bed protrusion segment (i.e., C5 segment), the eye segment (i.e., C5 segment), and the traffic segment (i.e., C6 segment).

In 520, the processing device 120 (e.g., the centerline determination module 420) (e.g., the processing circuits of the processor 210) may determine a centerline of a target object in the one or more based on the image data.

In some embodiments, the target object may be one of the one or more objects that need to be observed or recognized. In some embodiments, the target object may include a region of interest (ROI). In some embodiments, the target object may be each of the one or more objects. For example, the target object may be one of the tubular structures. As another example, the target object may be a blood vessel, the trachea, a nerve, or the like. In some embodiments, the target object may be determined manually by a user (e.g., a doctor) or automatically by the processing device 120. For example, the user may select or specify a target object from the one or more objects based on clinical experience. As another example, the processing device 120 may automatically recognize a target object from the image data based on a recognition algorithm (e.g., a region of interest (ROI) recognition algorithm, an image segmentation algorithm, etc.).

The centerline of the target object (also referred to as a target centerline) may refer to a geometric centerline of the target object along an extension direction of the target object. As used herein, the extension direction of an object may refer to a direction along which the length of the object is increased. The geometric centerline may include center points of cross sections of the target object perpendicular to the extension direction of the target object. In some embodiments, the target object may include a plurality of portions (or regions). Each of the plurality of portions may have a centerline segment. The centerline of the target object may be composed of a plurality of centerline segments of the plurality of portions. For example, if the target object is the vertebral artery, the centerline of the vertebral artery may include a centerline segment of the outer bone segment, a centerline segment of the intervertebral foramina segment, a centerline segment of the outer spinal segment, and a centerline segment of the intradural segment.

In some embodiments, the image data may include a plurality of 2D image layers. Each of the plurality of 2D image layers may include at least a part of the target object. The processing device 120 may extract a centerline (also referred to as slice centerline) of the at least a part of the target object in the 2D image layer. Further, the processing device 120 may determine the centerline (i.e., the geometric centerline) of the target object based on a plurality of slice centerlines corresponding to the plurality of 2D image layers. For example, the processing device 120 may superpose the plurality of slice centerlines to form the geometric centerline.

In some embodiments, the image data may include a 3D image, and the processing device 120 may determine the geometric centerline of the target object from the 3D image. For example, the processing device 120 may extract the centerline of the target object using various techniques, such as an automatic detection technique (e.g., a machine learning technique), a centerline path calculation technique, etc.

In some embodiments, using the centerline path calculation technique, the processing device 120 may extract the centerline of the target object by performing a centerline path calculation on the target object. For example, the processing device 120 may obtain a plurality of positioning points (e.g., X1, X2, . . . Xn) of the target object in the image data. The positioning points may be selected or specified by the user or determined according to a default setting of the system 100. Merely by way of example, a positioning point may be a center point of any cross section of the target object along the direction perpendicular to the extension direction of the target object. According to the plurality of positioning points, the processing device 120 may determine at least one candidate path. A candidate path may include the shortest path between any two positioning points or a path that may cover most positioning points. According to the determined at least one candidate path, the processing device 120 may determine the centerline of the target object. For example, the processing device 120 may assign any one of the at least one candidate path as the centerline of the target object. As another example, the processing device 120 may determine the centerline of the target object by combining the at least one candidate path. As a further example, the processing device 120 may select at least one target candidate path that may cover all positioning points from the at least one candidate path, and then determine the centerline of the target object by merging the at least one target candidate path.

In some embodiments, using the automatic detection technique, the processing device 120 may extract the centerline of the target object using a trained machine learning model (e.g., a trained neural network model). The trained machine learning model may be obtained by a processing device that is the same as or different from the processing device 120 online or offline. The processing device 120 may obtain the trained machine learning model from a storage device or the processing device. For example, the processing device may determine the trained machine learning model based on a plurality of training samples each of which includes a sample image includes an object and a reference image includes the object with marked centerlines. Specifically, in a training process, the sample image served as an input and the reference image served as a desired output may be input into a preliminary machine learning model and values of the parameters of the preliminary machine learning model may be updated based on a difference between an actual output generated based on the input to obtain the trained machine learning model. The trained machine learning model may be obtained in a similar manner as described in connection with FIG. 6, and the descriptions thereof are not repeated here.

In some embodiments, the processing device 120 may extract the centerline of the target object using a tracking technique. Specifically, the processing device 120 may determine a starting point of the target object and determine a centerline direction (i.e., the extension direction of the target object) based on gradient information of the starting point. Further, the processing device 120 may obtain a next point along the centerline direction. According to the next point and gradient information of the next point, the processing device 120 may continue to obtain a new centerline direction until an end point of the target object is reached. After the end point of the target object is reached, the processing device 120 may obtain a line by connecting all points (e.g., the starting point, the next point, the end point), and then process (e.g., smooth filtering) the line to determine a smooth line as the centerline of the target object. The starting point may refer to a point located at a beginning position of the target object. The end point may refer to a point located at an end position of the target object.

In some embodiments, the processing device 120 may extract the centerline of the target object using other techniques, such as a refinement algorithm. Specifically, the processing device 120 may identify and analyze the image data to remove simplified points. The simplified points may refer to points that do not change the topological properties of the object after being removed. After removing the simplified points, the processing device 120 may obtain a skeleton line that may maintain a connected structure and topological properties of the target object, and then assign the skeleton line as the centerline of the target object.

In some embodiments, the processing device 120 may directly extract the centerline of the target object from the image data. In some embodiments, the processing device 120 may segment the target object from the image data, and then extract the centerline based on the segmented target object, which may improve the accuracy of the extraction of the centerline of the target object. The processing device 120 may segment the target object from the image data using an image segmentation algorithm, or other segmentation manners. More descriptions of the extraction of the centerline of the target object may be found elsewhere in the present disclosure (e.g., FIG. 13 and the description thereof).

In 530, the processing device 120 (e.g., the recognition module 430) (e.g., the processing circuits of the processor 210) may determine a recognition result of the target object based on at least one feature parameter of the centerline of the target object using a trained neural network model. As used herein, a feature parameter may also be referred to as a feature. Performing an operation on a feature parameter may refer to performing an operation on a value of the feature parameter.

The at least one feature parameter of the target centerline may include size information of the target centerline, position information of the target centerline in the image data, position information of the target centerline in a centerline tree associated with the target centerline, information of the centerline tree associated with the target centerline, or the like, or any combination thereof.

In some embodiments, a centerline tree may refer to a tree structure composed of a plurality of centerlines of a plurality of objects in an image. Any one centerline in the centerline tree may be connected to at least one other centerline in the centerline tree. A centerline tree of a tubular structure may reflect the topology of a plurality of tubular structures associated with the tubular structure. In some embodiments, the centerline tree may include a main trunk and one or more branches. A connection point of each branch with the main trunk may be referred to as a root node. A connection point of any two branches may be referred to as a branch node. In some embodiments, the processing device 120 may determine a centerline tree by traversing and extracting a centerline from a main trunk of the tubular structure. In some embodiments, the processing device 120 may determine a centerline tree by registering image data (e.g., an image) with standard image data (e.g., a standard image) with a known centerline tree. Alternatively, the processing device 120 may determine a centerline tree using a trained model.

The size information of the target centerline may include a length (e.g., 10 mm) of the target centerline, a ratio of the length of the target centerline to a height or width of the image, a ratio of the area where the centerline is located in the image to the area of the image, a rank of the length of the target centerline in lengths of centerlines in the centerline tree, etc. The position information of the target centerline in the image data may include coordinates of each point on the target centerline in a coordinate system of the image data, a region where the target centerline is located (e.g., a brainstem area in the brain image), deflection angle information of the target centerline relative to a reference line in the image data, a distance between the target centerline and a boundary of the target object, etc. The deflection angle information may indicate a degree of each segment of the target centerline deviates from the reference line in the image. The reference line may include a line between a starting position and an ending position of the target object, an edge of the image data, a line parallel to the edge of the image, or a coordinate axis in the coordinate system of the image data, etc. The deflection angle information may include an angle between each segment of the target centerline and the reference line.

The position information of the target centerline in the centerline tree associated with the centerline may include distribution information of the target centerline in the centerline tree, the deflection angle ranking of the target centerline in the centerline tree, etc. The distribution information of the centerline in the centerline tree may include that the target centerline is the main trunk or a branch of the centerline tree. The centerline tree associated with the target centerline may include the target centerline of the target object and a reference centerline of at least one reference object associated with the target object among the one or more objects. The at least one reference object may refer to objects other than the target object in the image data or objects in the area where the target centerline of the target object is located. For example, the at least one reference object may include other tubular structures in the image data except the target tubular structure. In some embodiments, the reference centerline of the at least one reference object and the target centerline of the target object may be in the same centerline tree. In such cases, the target centerline of the target object and the reference centerline of the at least one reference object may form the centerline tree associated with the target centerline.

The information of the centerline tree associated with the target centerline may include information (e.g., feature parameters) of one or more reference centerlines in the centerline tree (also referred to as local features of the centerline tree), feature parameters of the centerline tree (also referred to as global features of the centerline tree), or a combination thereof. In some embodiments, the global feature parameter of a centerline tree may include a center of gravity of the centerline tree, a VOI of the centerline tree, topology parameters of the centerline tree, a diameter of the centerline tree, etc. The topology parameters of the centerline tree may include a count of root nodes in the centerline tree, a depth of the centerline tree, a count of branch nodes on each level or layer, a count of centerlines on each node, etc. The depth of the centerline tree may refer to a count of levels or layers in the centerline tree. A level or layer in the centerline tree may include one or more centerlines connected to a root node in the centerline tree and other centerlines connected to the one or more centerlines. The diameter of the centerline tree may refer to a distance between the two furthest nodes (e.g., root nodes, branch nodes). The local features of the centerline tree (i.e., feature parameters of a reference centerline) may be the same as or similar to the feature parameter of the target centerline and may be not repeated herein.

In some embodiments, the processing device 120 may determine a reference centerline of at least one reference object associated with the target object among the one or more objects based on the image data. The processing device 120 may determine the centerline tree based on the target centerline of the target object and the reference centerline associated with the centerline of the target object. Further, the processing device 120 may determine the feature parameter of the centerline tree. For example, the processing device 120 may determine the feature parameter of the centerline tree according to the feature parameter of the reference centerline. According to the at least one feature parameter of the target centerline of the target object and the at least one feature parameter of the centerline tree, the processing device 120 may determine the recognition result of the target object using the trained neural network model. The use of the trained neural network model may improve the efficiency and accuracy of the object recognition.

In some embodiments, the trained neural network model may be pre-trained and stored in a storage device (e.g., the storage device 150) disclosed elsewhere in the present disclosure. The processing device 120 may retrieve the trained neural network model from the storage device. The trained neural network model may include, but is not limited to, a feature extraction neural network, a feedforward neural network (FNN), a recurrent neural network (RNN), a long and short-term memory neural network (LSTM), or the like, or any combination thereof. The feature extraction neural network may include a convolutional neural network (CNN), a fully convolutional neural network (FCN), a recursive Neural network (RNN), or the like, or any combination thereof. Since neural networks have memory, parameter sharing, and Turing completeness, the neural networks may have certain advantages when learning the nonlinear characteristics of sequence data. The tubular structures in the image data may be staggered and complex and a plurality of tubular structures have strong relevance. The at least one feature parameter of a centerline of a tubular structure may include typical sequence data (e.g., coordinates). Therefore, the trained neural network model may be used to learn the name of the centerline according to the at least one feature parameter of the target centerline. In some embodiments, the trained neural network model may be any artificial neural network that may implement a deep learning algorithm. The artificial neural network has been proven to successfully implement data prediction-related applications, for example, data trend prediction and speech identification.

In some embodiments, the trained neural network model may be trained based on a plurality of training samples by a processing device that is the same as or different from the processing device 120 online or offline. The trained neural network model trained offline by the processing device may be stored in a storage device and the processing device 120 may obtain the trained neural network model from the storage device. More descriptions regarding the trained neural network model may be found elsewhere in the present disclosure (e.g., FIG. 6 and the description thereof).

In some embodiments, the processing device 120 may input the at least one feature parameter of the target centerline of the target object and/or the at least one feature parameter of the centerline tree into the trained neural network model, and then determine the recognition result of the target object based on an output of the trained neural network model. In this embodiment, a relationship between the target centerline and a centerline tree associated with the centerline may be considered to recognize the target centerline, which may improve the accuracy of the recognition of the centerline of the target object.

In some embodiments, before the at least one feature parameter of the target centerline of the target object and the at least one feature parameter of the centerline tree are input into the trained neural network model, the processing device 120 may preprocess the at least one feature parameter of the target centerline of the target object and the at least one feature parameter of the centerline tree. Merely by way of example, the preprocessing may include data bucketing, scoring, normalization, etc.

In some embodiments, other models, such as a logistic regression model, a support vector machine, a clustering model, a decision tree model, etc. may also be used to determine the recognition result of the target object. Taking the logistic regression model as an example, the processing device 120 may input the at least one feature parameter of the target centerline of the target object and/or the at least one feature parameter of the centerline tree into the logistic regression model, and then determine the recognition result of the target object based on an output of the logistic regression model.

In some embodiments, the recognition result may include the name of the target object. Merely by way of example, the name of the target object may include the anatomical structure name of the target object. For example, when the one or more objects in the image data are cerebral blood vessels, the recognition result of the target object may be the internal carotid artery. As another example, when the one or more objects in the image data are the trachea, the recognition result of the target object may be the upper lobe bronchus. As a further example, when one or more objects in the image data are cranial nerves, the recognition result of the target object may be the petrous nerve. In some embodiments, the recognition result of the target object may also include other information related to the target object, such as a function and structural characteristics of the target object.

As described in connection with FIG. 5, the target object may include a plurality of portions (or regions). In some embodiments, the at least one feature parameter of the target centerline of the target object may also include feature parameter of a centerline segment of each of the plurality of portions of the target object. In this embodiment, the processing device 120 may input the at least one feature parameter of the target centerline of the target object, the at least one feature parameter of the centerline tree, and/or the feature parameter of each of the centerline segments in the target centerline into the trained neural network model, and then determine the recognition result of the target object based on an output of the trained neural network model. The recognition result of the target object may include a name (e.g., an anatomical structure name) and/or a label of each of the plurality of portions of the target object. For example, for the vertebral artery in cerebral vessels, the recognition result of the target object may include the outer bone segment (i.e., V1 segment); the intervertebral foramina segment (i.e., V2 segment); the outer spinal segment (i.e., V3 segment); the intradural segment (i.e., V4 segment). The V1 segment may be a label of a portion of the vertebral artery named as the outer bone segment. The V2 segment may be a label of a portion of the vertebral artery named as the intervertebral foramina segment. The V3 segment may be a label of a portion of the vertebral artery named as the outer spinal segment. The V4 segment may be a label of a portion of the vertebral artery named as the intradural segment. In some embodiments, the recognition result of the target object may also include other information related to the plurality of portions of the target object, such as a function and structural characteristics of each of the plurality of portions of the target object.

In the present disclosure, a centerline of a target object (e.g., a tubular structure) may reflect a spatial topology (e.g., a spatial distribution) of the target object. Curved surface reconstruction (CPR) may be performed on the target object along the target centerline of the target object based on the recognition result of the target object and the image data, so that the user may view the full appearance of the target object along the target centerline. For example, the processing device 120 may reconstruct 2D image slices each of which represents a layer of the target object perpendicular to the target centerline. The 2D image slices may form a 3D image of the target object that represents the full appearance of the target object.

In 540, the processing device 120 (e.g., the abnormality determination module 440) (e.g., the processing circuits of the processor 210) may perform an anomaly detection on the target object based on the recognition result of the target object.

The processing device 120 may determine whether the target object includes an abnormality. The abnormality of the target object may include a structural abnormality (e.g., deformation, tissue defect, stenosis portion) of the target object compared with a standard structure (e.g., a normal structure), a component abnormality (e.g., tumors, stones, nodules, etc.) of the target object compared with a standard component (e.g., a normal component), etc.

In some embodiments, the processing device 120 may reconstruct a plurality of image slices (also referred to as reconstructed image slices) of the target object that represent layers of the target object that are substantially perpendicular to the target centerline based on the image data (e.g., one or more 2D image slices that represent layers of the target object that are substantially parallel to the target centerline). For each of the plurality of image slices, the processing device 120 may obtain at least one feature parameter of the target object from the image slice and determining whether the target object includes the abnormality based on the at least one feature parameter of the target object obtained from the image slice. More descriptions of the determination of whether the target object includes the abnormality may be found elsewhere in the present disclosure (e.g., FIG. 7 and the description thereof).

In some embodiments, the processing device 120 may determine whether the target object includes the abnormality by comparing the obtained 3D image of the target object and a standard anatomical model obtained based on the name of the target object. For example, the processing device 120 may determine a similarity between the obtained 3D image of the target object and the standard anatomical model. When the similarity exceeds a threshold, the processing device 120 may determine that the target object includes the abnormality. As used herein, the threshold may be default settings of the medical system 100 or may be adjustable under different situations. Different objects may correspond to different standard anatomical models. Various standard anatomical models may be pre-trained and stored in a storage device (e.g., the storage device 150) disclosed elsewhere in the present disclosure. The processing device 120 may retrieve the standard anatomical model from the storage device based on the name of the target object.

In response to determining that the target object includes the abnormality, the processing device 120 may determine location information of the abnormality based on the recognition result of the target object. For example, if it is determined that a target object has a tumor and the recognition result of the target object includes an anatomical name of the target object of the vertebral artery, the processing device 120 may determine that the tumor locates in the vertebral artery. In some embodiments, the processing device 120 may determine a portion among the plurality of portions (or regions) of the target object corresponding to the abnormality. Further, the processing device 120 may determine the location information of the abnormality based on the location information of the portion. For example, if it is further determined that the tumor exists in a portion of the target object and the recognition result of the target object includes an anatomical name of the portion is the outer bone segment and a label of the portion is the V1 segment, the processing device 120 may determine that the tumor locates in the outer bone segment in the vertebral artery.

In some embodiments, the processing device 120 may obtain multiple recognition results of multiple target objects according to operations 520 and 530. Each of the multiple recognition results of the multiple target objects may include a name of a target object. The processing device 120 may determine one of the multiple target objects based on the names of the multiple target objects and perform an analysis (e.g., a diagnosis or observation) on the determined target object. For example, the processing device 120 may determine the one of the multiple target objects based on an input of a user that is generated based on the names of the multiple target objects according to clinical requirements.

In some embodiments, the processing device 120 may determine whether the target object includes the abnormality based on a trained machine learning model for anomaly detection. For example, the processing device 120 may input each reconstructed image slice into the trained machine learning model for anomaly detection and the trained machine learning model for anomaly detection may output a result indicating whether the target object includes the abnormality, the type of the abnormality, the location of the abnormality, and/or other information associated with the abnormality. The trained machine learning model for anomaly detection may be obtained by a processing device that is the same as or different from the processing device 120 online or offline. For example, the processing device may obtain a plurality of training samples each of which includes an image slice and a label indicating whether an object represented in the image slice includes the abnormality. The processing device may train a preliminary machine learning model by updating parameter values of the preliminary machine learning model in each iteration by comparing an estimated output of the preliminary machine learning model and the label (i.e., a desired output). More descriptions for training the preliminary machine learning model may be found in FIG. 6 and the descriptions thereof. In some embodiments, different types of objects may correspond to different trained machine learning models for anomaly detection. The processing device 120 may determine the trained machine learning model for anomaly detection for the target object based on the name of the target object.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. For example, the process 500 may include an additional transmitting operation in which the processing device 120 may transmit the recognition result of the target object to the terminal device 130. As another example, the process 500 may include an additional storing operation in which the processing device 120 may store information and/or data (e.g., the image data, the at least one feature parameter of the centerline, the trained neural network model, the recognition result of the target object) associated with object recognition in a storage device (e.g., the storage device 150, the storage 220, the storage 390) disclosed elsewhere in the present disclosure.

Figure 6:
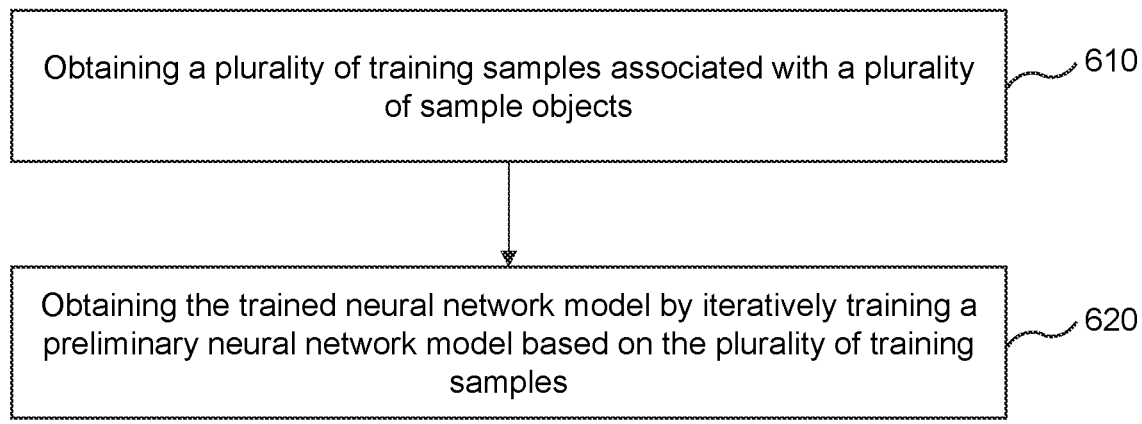
FIG. 6 is a flowchart illustrating an exemplary process for determining a trained neural network model according to some embodiment of the present disclosure.

FIG. 6 is a flowchart illustrating an exemplary process for determining a trained neural network model according to some embodiment of the present disclosure. In some embodiments, process 600 may be executed by the medical system 100. For example, the process 600 may be implemented as a set of instructions (e.g., an application) stored in a storage device (e.g., the storage device 150, the storage 220, and/or the storage 390). In some embodiments, the processing device 120 (e.g., the processor 210 of the computing device 200, the CPU 340 of the mobile device 300, and/or one or more modules illustrated in FIG. 4), the object recognition device 1200 (e.g., one or more units illustrated in FIG. 12), and/or the target tissue positioning device 1700 (e.g., one or more units illustrated in FIG. 17) may execute the set of instructions and may accordingly be directed to perform the process 600. Alternatively, the process 600 may be performed by a computing device of a system of a vendor that provides and/or maintains such a trained neural network model. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting.

In 610, the processing device 120 (e.g., the training module 460) (e.g., the processing circuits of the processor 210) may obtain a plurality of training samples associated with a plurality of sample objects.

In some embodiments, a sample object may include a tubular structure, such as blood vessels, the trachea, nerves, the large intestine, the small intestine, etc. More descriptions of the sample object may refer to the description of the object elsewhere in the present disclosure (e.g., operation 510 in FIG. 5 and the description thereof).

In some embodiments, at least one of the plurality of training samples may be previously generated and stored in a storage device (e.g., the storage device 150, the storage 220, the storage 390, or an external database). The processing device 120 may retrieve the training samples directly from the storage device.

In some embodiments, each of the plurality of training samples may include at least one feature parameter of a centerline of a sample object associated with the training sample and a name of the sample object. The processing device 120 may extract a centerline of each sample object in a sample image. Each sample image may include one or more sample objects. The sample image may refer to an image obtained based on a sample subject. For example, the sample image may be an image of a sample subject acquired by an imaging device (e.g., the imaging device 110). More descriptions of the sample subject may refer to the description of the subject elsewhere in the present disclosure (e.g., operation 510 in FIG. 5 and the description thereof). Further, the processing device 120 may label the centerline of the sample object with an anatomical name of the sample object and obtain the at least one feature parameter of the centerline of the sample object. More descriptions of the at least one feature parameter of the centerline of the sample object may refer to the description of the at least one feature parameter of the centerline of the target object elsewhere in the present disclosure (e.g., operation 530 in FIG. 5 and the description thereof).

In some embodiments, each of the plurality of training samples may also include at least one feature parameter (e.g., the global feature and/or the local feature) of a centerline tree corresponding to a sample object associated with the training sample. The processing device 120 may determine a centerline tree associated with the sample object based on the centerline of the sample object. The centerline tree associated with the sample object may include the centerline of the sample object and a reference centerline of at least one reference object associated with the sample object. More descriptions of the reference centerline and the reference object may be found elsewhere in the present disclosure (e.g., operation 530 in FIG. 5 and the description thereof). Further, the processing device 120 may obtain the at least one feature parameter of the centerline tree. More descriptions of the at least one feature parameter of the centerline tree may be found elsewhere in the present disclosure (e.g., operation 530 in FIG. 5 and the description thereof).

In 620, the processing device 120 (e.g., the training module 460) (e.g., the processing circuits of the processor 210) may obtain the trained neural network model by iteratively training a preliminary neural network model based on the plurality of training samples.

As described in connection with FIG. 5, the trained neural network model may include, but is not limited to, a feature extraction neural network (e.g., a convolutional neural network (CNN), a fully convolutional neural network (FCN), a recursive Neural network (RNN)), a feedforward neural network (FNN), a recurrent neural network (RNN), a long and short-term memory neural network (LSTM), or the like, or any combination thereof. In some embodiments, the preliminary neural network model may include at least one model parameter. A preliminary value of the at least one model parameter may be a default setting of the medical system 100 or may be adjustable under different situations. Take a CNN model as an example, the at least one model parameter may include a count of convolutional layers, a count of kernels, a kernel size, a stride, a padding of each convolutional layer, or the like, or any combination thereof.

In some embodiments, the processing device 120 may train the preliminary neural network model based on an algorithm, such as a gradient descent algorithm. Exemplary gradient descent algorithms may include an Adam optimization algorithm, a stochastic gradient descent (SGD)+ Momentum optimization algorithm, a Nesterov accelerated gradient (NAG) algorithm, an Adaptive Gradient (Adagrad) algorithm, an Adaptive Delta (Adadelta) algorithm, a Root Mean Square Propagation (RMSprop) algorithm, an AdaMax algorithm, a Nadam (Nesterov-accelerated Adaptive Moment Estimation) algorithm, an AMSGrad (Adam+ SGD) algorithm, or the like, or any combination thereof.

In some embodiments, the processing device 120 may train the preliminary neural network model iteratively until a termination condition is satisfied. In response to that the termination condition is satisfied, the preliminary neural network model may be finalized. In some embodiments, the termination condition may relate to a value of a loss function. The loss function may be a default setting of the medical system 100 or may be adjustable under different situations. For example, the loss function may include a cross entropy loss function, a mean square error (MSE) loss function, etc. Merely by way of example, the termination condition may be satisfied if the value of the loss function is minimal or smaller than a predetermined threshold. As another example, the termination condition may be satisfied if the value of the loss function converges. In some embodiments, "convergence" may refer to that the variation of the values of the loss function in two or more consecutive iterations is equal to or smaller than a predetermined threshold. In some embodiments, "convergence" may refer to that a difference between the value of the loss function and a target value is equal to or smaller than a predetermined threshold. In some embodiments, the termination condition may be satisfied when a specified count of iterations have been performed in the training process.

In each iteration, at least one feature parameter of a centerline of a sample object and/or at least one feature parameter of a centerline tree corresponding to the sample object may be used as an input of the preliminary neural network model. A name of the sample object may be used as a reference output of the preliminary neural network model. Values (e.g., preliminary values) of model parameters of the preliminary neural network model may be updated by comparing the reference output and an estimated output of the preliminary neural network model generated based on the input of the preliminary neural network model. In some embodiments, the values of model parameters of the preliminary neural network model may be updated by an error back propagation manner.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, the processing device 120 may update the trained neural network model periodically or irregularly based on one or more newly-generated training samples (e.g., new sample images). As another example, the processing device 120 may divide the plurality of training samples into a training set and a test set. The training set may be used to train the model and the test set may be used to determine whether the training process has been completed.

Figure 7:
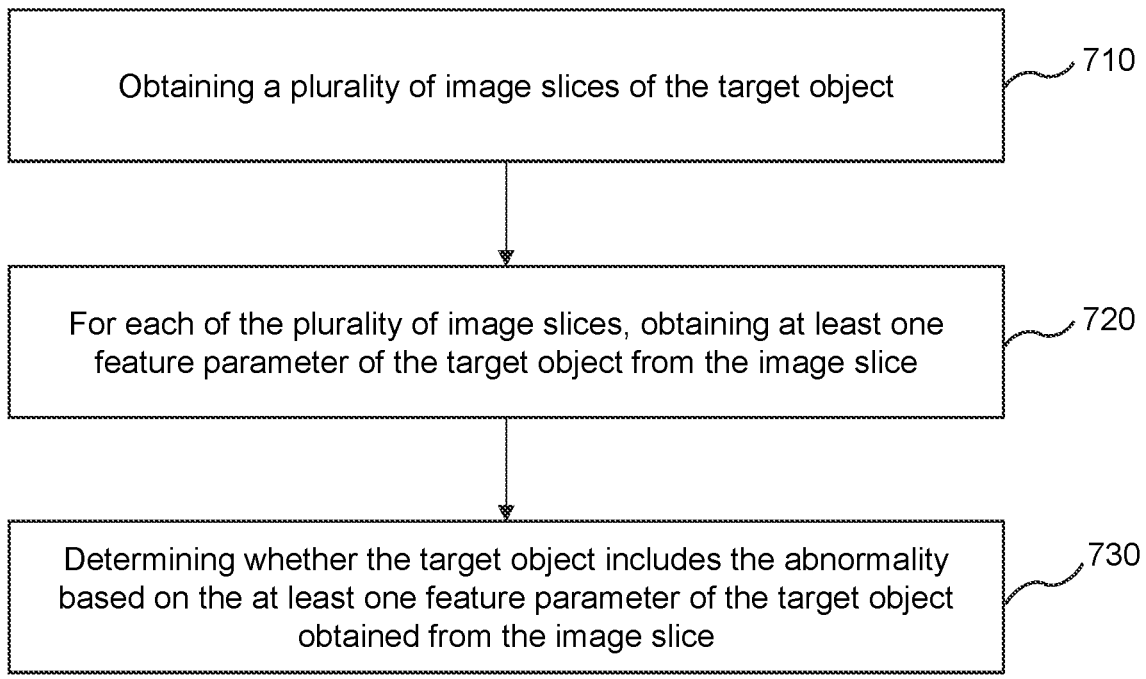
FIG. 7 is a flowchart illustrating an exemplary process for determining whether a target object includes an abnormality according to some embodiments of the present disclosure.

FIG. 7 is a flowchart illustrating an exemplary process for determining whether a target object includes an abnormality according to some embodiments of the present disclosure. In some embodiments, process 700 may be executed by the medical system 100. For example, the process 700 may be implemented as a set of instructions (e.g., an application) stored in a storage device (e.g., the storage device 150, the storage 220, and/or the storage 390). In some embodiments, the processing device 120 (e.g., the processor 210 of the computing device 200, the CPU 340 of the mobile device 300, and/or one or more modules illustrated in FIG. 4), the object recognition device 1200 (e.g., one or more units illustrated in FIG. 12), and/or the target tissue positioning device 1700 (e.g., one or more units illustrated in FIG. 17) may execute the set of instructions and may accordingly be directed to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting.

In 710, the processing device 120 (e.g., the abnormality determination module 440) (e.g., the processing circuits of the processor 210) may obtain a plurality of image slices of the target object.

The processing device 120 may obtain the plurality of image slices of the target object along the centerline of the target object, and each of the plurality of image slices may represent a layer of the target object in a direction perpendicular to the centerline of the target object. As used herein, an image slice representing a layer of the target object in a direction (also referred to as a second direction) perpendicular to the centerline of the target object may also be referred to as that the image slice perpendicular to the centerline of the target object.

In some embodiments, the plurality of image slices may be obtained based on a plurality of image slices representing a layer of the target object in a first direction. For example, as described in connection with operation 510 in FIG. 5, the plurality of image slices of the target object may be reconstructed based on the image data of the subject obtained in 510. For example, as described in connection with FIG. 5, the processing device 120 may obtain a 3D image of the target object by performing a curved surface reconstruction (CPR) based on the image data of the subject (i.e., the plurality of image slices in the first direction). Further, the processing device 120 may extract the plurality of image slices perpendicular to the centerline of the target object along the centerline of the target object from the 3D image of the target object. As another example, the processing device 120 may obtain the plurality of image slices of the target object along the centerline of the target object using a certain interpolation manner.

In 720, for each of the plurality of image slices, the processing device 120 (e.g., the abnormality determination module 440) (e.g., the processing circuits of the processor 210) may obtain at least one feature parameter of the target object from the image slice.

In some embodiments, the target object may include a tubular structure and the tubular structure may include a tube having a lumen and a tube wall. The at least one feature parameter of the target object may include a structural parameter and/or a component parameter of the tubular structure. The structural parameter of the tubular structure may include a size of the tubular structure, such as a length of the pipe, a diameter of the lumen, a thickness of the tube wall, an area of the lumen, an area of the pipe wall, etc. The component parameter of the tubular structure may include components and/or component ratios (e.g., a water-fat ratio) in the tubular structure, etc.

In some embodiments, the processing device 120 may segment the image slice to identify the target object from the image slice. Further, the processing device 120 may determine the at least one feature parameter of the target object from the identified target object. For example, the processing device 120 may extract the structural parameter (e.g., the structural parameter of the tubular structure) from the obtained target object. As another example, the processing device 120 may determine the component parameter of the tubular structure based on pixel values (e.g., gray values) of the target object in the image data.

In 730, the processing device 120 (e.g., the abnormality determination module 440) (e.g., the processing circuits of the processor 210) may determine whether the target object includes the abnormality based on the at least one feature parameter of the target object obtained from the image slice.

In some embodiments, when the target object is the tubular structure, the processing device 120 may perform a tube diameter analysis on the tubular structure based on the at least one structural parameter of the lumen or the tube wall of the tubular structure. The processing device 120 may perform the tube diameter analysis by comparing the at least one structural parameter (or component parameter) with standard reference information (e.g., normal structural parameters, normal component parameters). For example, the processing device 120 may compare the diameter of the lumen with the normal diameter in the standard reference information to obtain a tube diameter analysis result, for example, the tube diameter is too small, the tube diameter is too large. As another example, the processing device 120 may compare components of the tube wall with normal components in the standard reference information to obtain a tube diameter analysis result, for example, whether the tubular structure has abnormal components (e.g., a plaque). As a further example, the processing device 120 may compare the water-fat ratio of the tube wall with a normal water-fat ratio in the standard reference information to obtain a tube diameter analysis result, for example, abnormal water-fat ratio. The water-ratio of the tube wall may be determined based on pixel values of the target object represented in an image slice.

According to the tube diameter analysis result, the processing device 120 may determine whether the target object includes the abnormality. For example, the processing device 120 may identify a stenosis portion of the tubular structure based on the tube diameter analysis result. Specifically, when the tube diameter analysis result corresponding to an image slice indicates that the tube diameter is too small, e.g., smaller than a threshold (e.g., an average tube diameter), the processing device 120 may determine a portion of the tubular structure corresponding to the image slice may be a stenosis portion of the tubular structure. In some embodiments, when the stenosis portion exists in the tubular structure, the processing device 120 may determine that the target object includes the abnormality. In some embodiments, the processing device 120 may further identify components (e.g., components of the tube wall in the stenosis portion, components between the tube wall and the lumen in the stenosis portion) associated with the stenosis portion to determine whether the tubular structure (e.g., the stenosis portion) includes an abnormal component. When the tubular structure includes the abnormal component, the processing device 120 may determine that the target object (e.g., the stenosis portion) includes the abnormality. As another example, according to the tube diameter analysis result, the processing device 120 determines that the tubular structure has a plaque. Further, the processing device 120 may determine whether the plaque includes an abnormality by analyzing the composition of the plaque. Merely by way of example, the processing device 120 may determine whether the plaque is a hard plaque or a soft plaque. As another example, the processing device 120 may determine whether the plaque is calcified, lipid, fibrous cap, or bleeding.

In some embodiments, the processing device 120 may perform further analysis on the abnormality to obtain more detailed information of the abnormality, which may facilitate the use of clinical medicine and medical research. In the present disclosure, the abnormality in the target object may be automatically determined and analyzed along the centerline of the target object, which may improve the efficiency and accuracy of the tubular structure analysis. More descriptions regarding the determination of whether the target object includes the abnormality may be found elsewhere in the present disclosure (e.g., FIG. 14 and the description thereof).

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 700 may be accomplished with one or more additional operations not described and/or without one or more of the operations discussed above.

Figure 8:
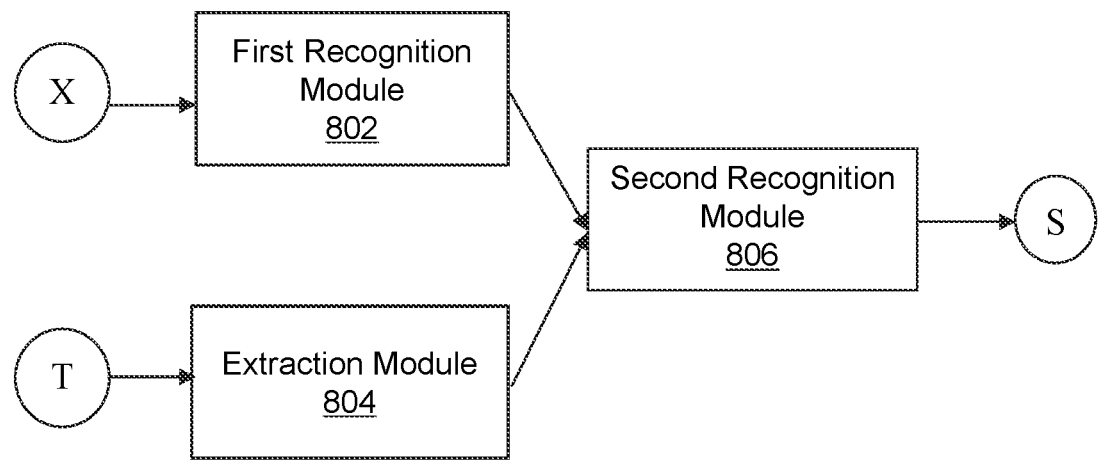
FIG. 8 is a schematic diagram illustrating an exemplary trained neural network model according to some embodiments of the present disclosure.

FIG. 8 is a schematic diagram illustrating an exemplary trained neural network model according to some embodiments of the present disclosure. As shown in FIG. 8, the trained neural network model 800 may include a first recognition module 802, an extraction module 804, and a second recognition module 806.

In some embodiments, the first recognition module 802 may be configured to determine a preliminary recognition result of a target object (e.g., a tubular structure) based on the at least one feature parameter (donated as X) of a centerline of the target object (also referred to as target centerline). The first recognition module 802 may be configured to determine the preliminary recognition result of the target object based on at least one feature parameter of the target centerline of the target object obtained from image data of the target object. In some embodiments, the target object may include a plurality of portions. The target centerline may include segments (i.e., centerline segments) each of which corresponds to one of at least one of the plurality of portions in the target object. The first recognition module 802 may determine the preliminary recognition result based on feature parameters of each of at least a portion of the centerline segments (also referred to as local features of the target centerline) and/or feature parameters of the target centerline (also referred to as global features of the target centerline).

In some embodiments, the first recognition module 802 may include a feedforward neural network (FNN), a recurrent neural network (RNN), a long short-term memory neural network (LSTM), or the like, or any combination thereof. In some embodiments, the at least one feature parameter of the target centerline and/or the at least one feature parameter of each centerline segment in the target centerline may be input into the first recognition module 802, and then the preliminary recognition result of the target object may be determined based on an output of the first recognition module 802. More descriptions regarding the RNN may be found elsewhere in the present disclosure (e.g., FIG. 9 and the description thereof).

In some embodiments, the first recognition module 802 may be configured to process feature parameters of the target centerline. For example, the first recognition module 802 may be configured to form a feature vector based on the feature parameters of the target centerline. As another example, the first recognition module 802 may be configured to preprocess, such as bucket, score, normalize, etc., the feature parameters of the target centerline.

The extraction module 804 may be configured to determine at least one feature parameter of a centerline tree (donated as T) corresponding to the target centerline. In some embodiments, feature parameters of centerlines in the centerline tree may be input into the extraction module 804 and the at least one feature parameter of the centerline tree may be determined based on an output of the extraction module 804. Specifically, the extraction module 804 may linearly combine the feature parameters of the centerlines in the centerline tree, and then perform feature mapping on the combined feature parameters to determine the at least one feature parameter of the centerline tree. The feature mapping may be performed by using a nonlinear activation function.

In some embodiments, the extraction module 804 may include a mathematical model, a neural network model (e.g., a recursive neural network model), or the like, or any combination thereof. For example, the recursive neural network model may include a plurality of nodes. The structure of the recursive neural network model may be the same as or similar to the structure of the centerline tree. The extraction module 804 may be configured to determine the at least one feature parameter of the centerline tree by inputting at least one feature parameter of each centerline in the centerline tree into one of the plurality of nodes corresponding to the centerline in the centerline tree. The use of the recursive neural network model that has the same structure as the centerline tree may improve the efficiency and accuracy of determining the at least one feature parameter of the centerline tree. More descriptions regarding the recursive neural network model may be found elsewhere in the present disclosure (e.g., FIG. 10 and the description thereof).

The second recognition module 806 may be configured to determine the recognition result (denoted as S) of the target object based on the output (e.g., the preliminary recognition result, or the processed feature parameter of the target centerline) of the first recognition module 806 and the at least one feature parameter of the centerline tree. In some embodiments, the second recognition module 806 may include a deep neural network model, a mathematical model, or the like, or any combination thereof. In some embodiments, the preliminary recognition result and the at least one feature parameter of the centerline tree may be input into the second recognition module 806 and the recognition result of the target object may be determined based on an output of the second recognition module 806.

Figure 9:
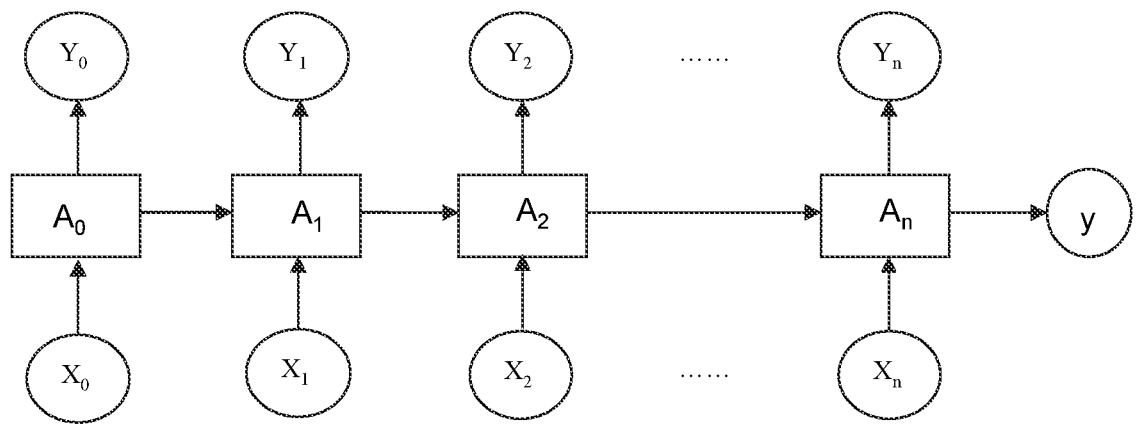
FIG. 9 is a schematic diagram illustrating an exemplary trained machine learning model according to some embodiments of the present disclosure.

FIG. 9 is a schematic diagram illustrating an exemplary trained machine learning model according to some embodiments of the present disclosure. In some embodiments, the first recognition module 802 as shown in FIG. 8 may be the same as or similar to the trained machine learning model as shown in FIG. 9.

The trained machine learning model may be constructed based on a recurrent neural network. The trained machine learning model may be configured to determine a recognition result of a target object (e.g., a tubular structure) based on at least one feature parameter of a centerline of the target object (also referred to as target centerline). In some embodiments, the target object may include a plurality of portions. The target centerline may include portions or segments (i.e., centerline segments) each of which corresponds to one of at least one of the plurality of portions in the target object. The trained machine learning model may determine the preliminary recognition result based on feature parameters of each of at least a portion of the centerline segments (also referred to as local features of the target centerline). The centerline segments of the target centerline may be determined by a user or according to a default setting of the system 100. For example, the centerline segments of the target centerline may be determined to have the same length or according to anatomical structures of the target object.

As shown in FIG. 9, the recurrent neural network may include n (n is an integer greater than 1) neurons (e.g., $A_0$, $A_1$, $A_2$, ..., $A_n$) (also referred to as nodes). The n neurons may connect to each other and each neuron may correspond to a network weight. In some embodiments, feature parameters of the target centerline may be a sequence of data, such as the coordinates of points in the target centerline. The plurality of portions of the target centerline (i.e., centerline segments) may be donated as $X_0$, $X_1$, $X_2$, ..., $X_n$. Feature parameters of each portion of the centerline may be input into a neuron corresponding to the portion of the target centerline. For example, feature parameters of a portion $X_0$ may be input into the neuron $A_0$, feature parameters of a portion $X_1$ may be input into the neuron $A_1$, feature parameters of a portion $X_2$ may be input into the neuron $A_2, \ldots$, feature parameters of a portion $X_n$ may be input into the neuron $A_n$. In some embodiments, each neuron may generate an output based on the input, and the output may be a recognition result of a portion of the target centerline. For example, the neuron $A_0$ may output a recognition result $Y_0$ of the portion $X_0$, the neuron $A_1$ may output a recognition result $Y_1$ of the portion $X_1$, the neuron $A_2$ may output a recognition result $Y_2$ of the portion $X_2, \ldots$ the neuron $A_n$ may output a recognition result $Y_n$ of the portion $X_n$. In some embodiments, the recurrent neural network may output the preliminary recognition result (denoted as y) of the target object based on the input of all neurons (e.g., $A_0, A_1, A_2, \ldots, A_n$). In some embodiments, the recurrent neural network may not generate outputs $Y_0, Y_1, Y_2, \ldots, Y_n$.

Figure 10:
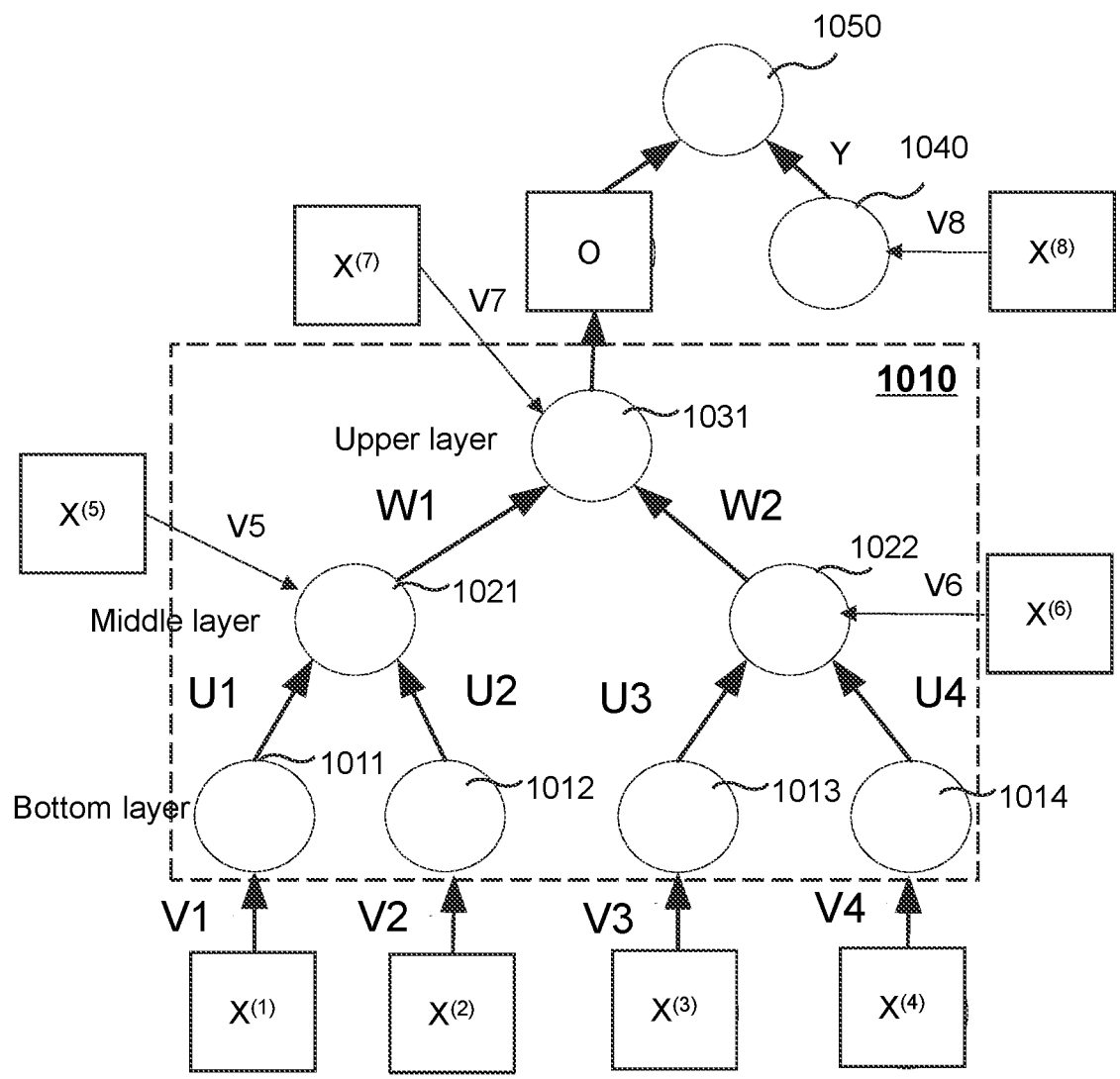
FIG. 10 is a schematic diagram illustrating an exemplary trained neural network model according to some embodiments of the present disclosure.

FIG. 10 is a schematic diagram illustrating an exemplary trained neural network model according to some embodiments of the present disclosure. As shown in FIG. 10, the trained neural network model 1000 may include a first recognition module 1040, an extraction module 1010, and a second recognition module 1050. The extraction module 1010 may include a recursive neural network model.

The recursive neural network model 1010 may be used to determine the at least one feature parameter of a centerline tree. The topological structure (e.g., a distribution of nodes) of the recursive neural network model 1010 may be the same as or similar to the topological structure of the centerline tree.

As shown in FIG. 10, the recursive neural network model 1010 may include a plurality of nodes (e.g., 1011, 1012, 1013, 1014, 1021, 1022, 1031). The plurality of nodes may include parent nodes and child nodes. In some embodiments, the recursive neural network model 1010 may include a plurality of layers. For example, as shown in FIG. 10, the recursive neural network model 1010 may include a bottom layer, a middle layer, and an upper layer. The nodes in the bottom layer may be parent nodes of the nodes in the middle layer and the nodes in the middle layer may be child nodes of the nodes in the bottom layer. The nodes in the middle layer may be parent nodes of the nodes in the upper layer and the nodes in the upper layer may be child nodes of the nodes in the middle layer. An output of at least one parent node may be used as an input of a child node. For example, the nodes 1011 and 1012 may be parent nodes of the node 1021 and the node 1021 may be a child node of the nodes 1011 and 1012. As another example, the node 1021 may be a parent node of the nodes 1031 and the node 1031 may be a child node of the node 1021.

A structure of the recurrent neural network model 1010 may be set according to the structure of the centerline tree. For example, a line between a parent node and a child node may be equivalent to a centerline in the centerline tree. The at least one feature parameter of the centerline may be used as the input of the parent node.

In some embodiments, the at least one feature parameter of each of the centerlines in the centerline tree may be input into a node corresponding to the centerline in the centerline tree to determine the at least one feature parameter of the centerline tree. A feature parameter of a centerline may be input into a node in the bottom layer and processed to output first-level information. The first-level information may be input into a node (e.g., a child node of the node the bottom layer) in the middle layer. The first-level information and a feature parameter of the centerline that is input into the node in the middle layer may be processed to output second-level information. The second-level information may be input into a node (e.g., a child node of the node in the middle layer) in the upper layer. The second-level information and a feature parameter of the centerline that is input into the node in the upper layer may be processed to output a feature parameter of the centerline tree.

Take a centerline tree including 8 centerlines (e.g., $x^{(1)}, x^{(2)}, x^{(3)}, x^{(4)}, x^{(5)}, x^{(6)}, x^{(7)}, x^{(8)}$) as an example, centerline $x^{(8)}$ may be the centerline of the target object, and the recurrent neural network model 1010 may include at least 7 nodes (e.g., 1011, 1012, 1013, 1014, 1021, 1022, 1031 each of which corresponds to a centerline of the centerline tree.

For example, a vector V1 that indicates the at least one feature parameter of the centerline $x^{(1)}$ may be input into the node 1011 and the node 1011 may generate a vector U1 based on vector V1. A vector V2 that indicates the at least one feature parameter of the centerline $x^{(2)}$ may be input into the node 1012 and the node 1012 may generate a vector U2 based on vector V2. A vector V3 that indicates the at least one feature parameter of the centerline $x^{(3)}$ may be input into the node 1013 and the node 1013 may generate a vector U3 based on vector V3. A vector V4 that indicates the at least one feature parameter of the centerline $x^{(4)}$ may be input into the node 1014 and the node 1014 may generate a vector U4 based on vector V4. The vectors U1 and U2 and a vector V5 that indicates the at least one feature parameter of the centerline $x^{(5)}$ may be input into the node 1021 and the node 1021 may generate a vector W1 based on vectors U1 and U2 and the vector V5. The vectors U3 and U4 and a vector V6 that indicates the at least one feature parameter of the centerline $x^{(6)}$ may be input into the node 1022 and the node 1022 may generate a vector W2 based on vectors U3 and U4 and the vector V6. Further, the vectors W1 and W2 and a vector V7 that indicates the at least one feature parameter of the centerline $x^{(7)}$ may be input into the node 1031 and the node 1031 may generate a vector O that indicates the at least one feature parameter of the centerline tree based on vectors W1 and W2 and the vector V7.

In some embodiments, the recurrent neural network model 1010 including 7 nodes may be used to determine the at least one feature parameter of the centerline tree including less than 8 centerlines. For example, for a centerline tree including 7 centerlines, each of the 7 centerlines including the centerline of the target object may be input one of the 7 nodes. As another example, for a centerline tree including less than 7 centerlines, each of centerlines in the centerline tree may be input any one of the 7 nodes.

A vector Y that indicates the preliminary recognition result of the target object may be obtained by inputting the vector V8 that indicates the at least one feature parameter of the centerline $x^{(8)}$ into the first recognition module 1040. Further, the vector O and the vector Y may be input into the second recognition module 1050 to obtain the recognition result of the target object.

Figure 11:
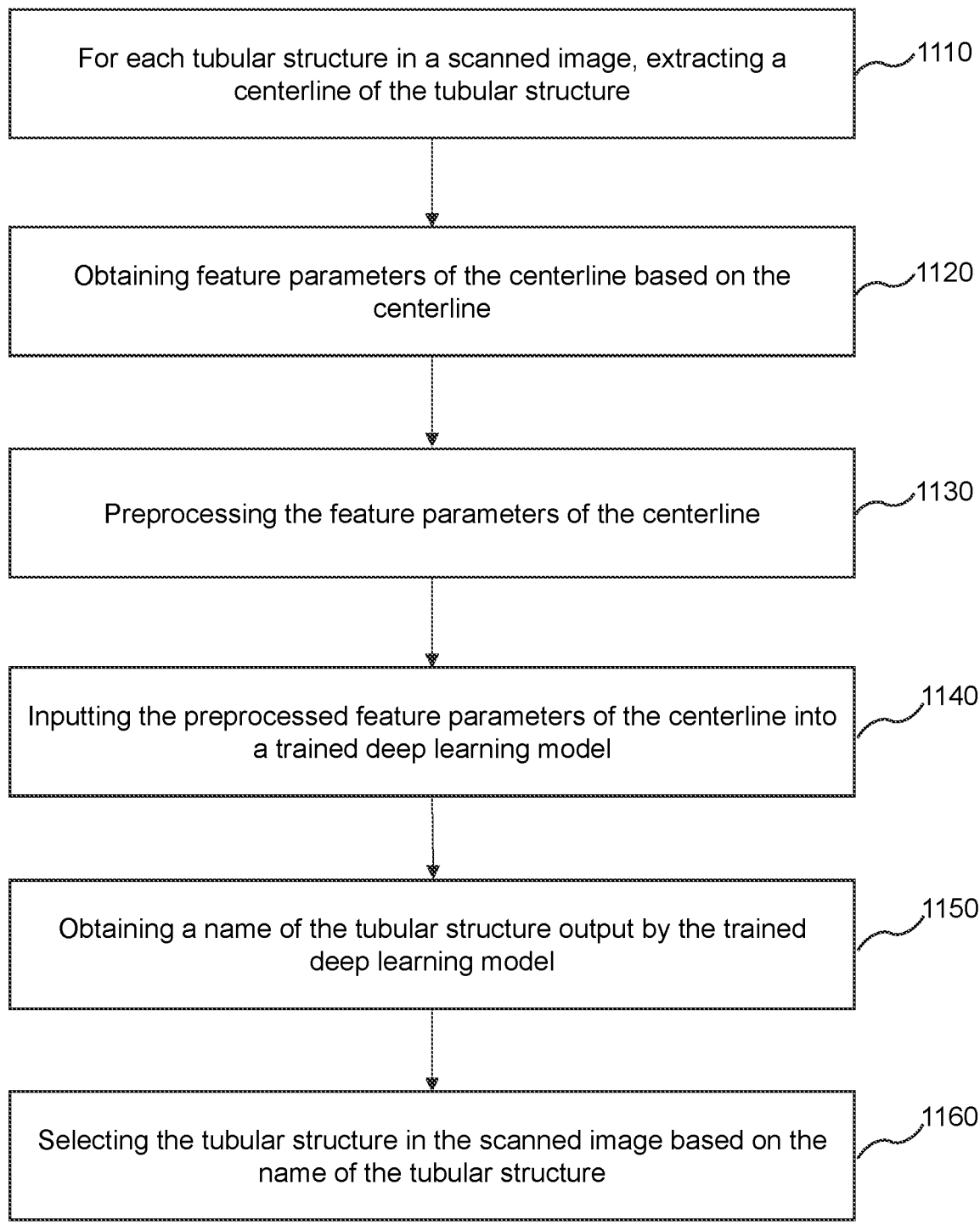
FIG. 11 is a flowchart illustrating an exemplary process for recognizing a tubular structure according to some embodiments of the present disclosure.

FIG. 11 is a flowchart illustrating an exemplary process for recognizing a tubular structure according to some embodiments of the present disclosure. In some embodiments, process 1100 may be executed by the medical system 100. For example, the process 1100 may be implemented as a set of instructions (e.g., an application) stored in a storage device (e.g., the storage device 150, the storage 220, and/or the storage 390). In some embodiments, the processing device 120 (e.g., the processor 210 of the computing device 200, the CPU 340 of the mobile device 300, and/or one or more modules illustrated in FIG. 4) and/or an object recognition device 1200 (e.g., one or more units illustrated in FIG. 12) illustrated in FIG. 12 may execute the set of instructions and may accordingly be directed to perform the process 1100. The operations of the illustrated process presented below are intended to be illustrative. In some embodiments, the process 1100 may be accomplished with one or more additional operations not described and/or without one or more of the operations discussed. Additionally, the order of the operations of process 1100 illustrated in FIG. 11 and described below is not intended to be limiting.

In 1110, for each tubular structure in a scanned image, a centerline of the tubular structure may be extracted. The scanned image may be an example of the image data captured by the imaging device disclosed elsewhere in the present disclosure. In some embodiments, operation 1110 may be performed by the processing device 120 (e.g., the centerline determination module 420 illustrated in FIG. 4) (e.g., the processing circuits of the processor 220) and/or the object recognition device 1200 (e.g., an extraction unit 1210 illustrated in FIG. 12).

The tubular structure may refer to tissue and/or an organ with a tubular structure, for example, a coronary artery in the heart, a cerebral vessel, a pulmonary artery, a bronchus, or the like, or any combination thereof. In some embodiments, the centerline of the tubular structure may be directly extracted from the scanned image. In some embodiments, one or more tubular structures may be segmented from the scanned image. Merely by way of example, the one or more tubular structures may be segmented from the scanned image by using an image segmentation algorithm. It is understood that this example described herein is not intended to be limiting. Further, for each of the one or more tubular structures, a centerline of the tubular structure may be extracted from the segmented tubular structure, which may improve the accuracy of the extraction of the centerline.

In 1120, feature parameters of the centerline may be obtained based on the centerline. In some embodiments, operation 1120 may be performed by the processing device 120 (e.g., the centerline determination module 420 illustrated in FIG. 4) (e.g., the processing circuits of the processor 220) and/or the object recognition device 1200 (e.g., a first obtaining unit 1220 illustrated in FIG. 12).

The feature parameters of the centerline may include coordinates of each point on the centerline and/or information associated with a centerline tree including the centerline. The coordinates of each point on the centerline may include coordinates of each pixel representing the point on the centerline in the scanned image. The centerline tree may be composed of centerlines corresponding to a plurality of tubular structures. For example, the centerline tree may be composed of centerlines of all tubular structures in the scanned image. The information associated with the centerline tree may include but is not limited to a center of gravity of the centerline tree and a region of interest (ROI) in the centerline tree.

In 1130, the feature parameters of the centerline may be preprocessed. In some embodiments, operation 1130 may be performed by the processing device 120 (e.g., the centerline determination module 420 illustrated in FIG. 4) (e.g., the processing circuits of the processor 220) and/or the object recognition device 1200 (e.g., a preprocessing unit 1230 illustrated in FIG. 12).

In some embodiments, the feature parameters of the centerline may be preprocessed. For example, the coordinates of each point on the centerline tree may be normalized according to the information associated with the centerline tree. Specifically, coordinates of each point on each centerline in the centerline tree may be normalized based on the center of gravity of the centerline tree, which may reduce the interference of noises, thereby improving the accuracy of the recognition of the tubular structure. The preprocessed feature parameters (e.g., the coordinates of points on the centerline) may conform to a standard normal distribution, that is, a mean of the coordinates of points on the centerline tree is 0 and a standard deviation of the coordinates of points on the centerline tree is 1.

In 1140, the preprocessed feature parameters of the centerline may be input into a trained deep learning model. In some embodiments, operation 1140 may be performed by the processing device 120 (e.g., the recognition module 430 illustrated in FIG. 4) (e.g., the processing circuits of the processor 220) and/or the object recognition device 1200 (e.g., an input unit 1240 illustrated in FIG. 12). The trained deep learning model may be an example of the trained neural network model disclosed elsewhere in the present disclosure. The trained deep learning model may be obtained in a similar manner as described in connection with FIG. 8, and the descriptions thereof are not repeated here. More descriptions regarding the trained neural network model may be found elsewhere in the present disclosure. See, e.g., FIG. 5, FIG. 8, and the description thereof.

In 1150, a name of the tubular structure output by the trained deep learning model may be obtained. In some embodiments, operation 1150 may be performed by the processing device 120 (e.g., the recognition module 430 illustrated in FIG. 4) (e.g., the processing circuits of the processor 220) and/or the object recognition device 1200 (e.g., a second obtaining unit 1250 illustrated in FIG. 12).

In 1160, a target tubular structure may be selected in the scanned image based on the names of the tubular structures in the scanned image. In some embodiments, operation 1160 may be performed by the processing device 120 (e.g., the recognition module 430 illustrated in FIG. 4) (e.g., the processing circuits of the processor 220) and/or the object recognition device 1200 (e.g., a selection unit 1260 illustrated in FIG. 12). The name of each tubular structure may be determined in operation 1150. The processing device 120 may determine the target tubular structure from the tubular structures in the scanned images based on the names of the tubular structures in the scanned image. For example, the processing device 120 may determine the target tubular structure according to an input of a user that is generated by the user based on the names of the tubular structures in the scanned image.

In some embodiments, the name of a tubular structure may be determined based on three-dimensional coordinates of the centerline of the tubular structure by a series of hierarchical logical judgments. For example, if the tubular structure is determined to be on a left side of a human body based on the three-dimensional coordinates of the centerline of the tubular structure, the tubular structure may be a left coronary artery. If the tubular structure is determined to be on a right side of the human body based on the three-dimensional coordinates of the centerline of the tubular structure, the tubular structure may be a right coronary artery. Then, coronary blood vessels in the left coronary artery or the right coronary artery may be recognized according to a manner, for example, identifying the longest blood vessel based on coordinates of the coronary blood vessels. However, the human body is very different, for example, different people may have different coronary blood vessels. The above mentioned differences may be even greater when people are sick. The above hierarchical logical judgments may be too complicated to be applicable for the many situations. Further, the hierarchical logical judgments may be suitable for the coronary artery and cannot be applicable for other tubular structures, for example, blood vessels, the trachea, and other tissues or organs.

In some embodiments, centerlines of a coronary artery may be manually marked based on multiple coronary artery images. An average image and an average model of the centerlines of the coronary artery may be generated by registering the multiple coronary artery images. Further, an image to be recognized may be registered with the average image to obtain the matching between the average model and the image to be recognized. Then, a similarity between a centerline in the image to be recognized and each centerline in the average model may be determined. A name of a centerline in the average model with the greatest similarity may be designated as a name of the centerline on the image to be recognized. Accordingly, human body differences may be taken into consideration when the average model is obtained, but there are still some shortcomings. For example, the matching between the average model and the image to be recognized may be not accurate, which may reduce the accuracy of similarities between the centerline on the image to be recognized and centerlines in the average model, thereby leading to misidentification.

In the present disclosure, for each tubular structure in the scanned image, the centerline of the tubular structure may be extracted. According to the centerline, the feature parameters of the centerline may be obtained. The feature parameters of the centerline may be preprocessed. The preprocessed feature parameters of the centerline may be input into the trained deep learning model. The name of the tubular structure output by the trained deep learning model may be obtained. Further, a target tubular structure may be selected from multiple tubular structures in the scanned image based on the names of the tubular structures. Accordingly, the trained deep learning model may be used to recognize the name of the centerline of the tubular structure in the present disclosure, which may reduce the calculation workflow and be suitable for each kind of tissues and organs. In addition, when the feature parameters of the centerline are obtained, the information associated with the centerline tree may be considered to recognize the name of the tubular structure, which may increase the accuracy of the recognition of the tubular structure.

It should be noted that the above description regarding the process 1100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted.

Figure 12:
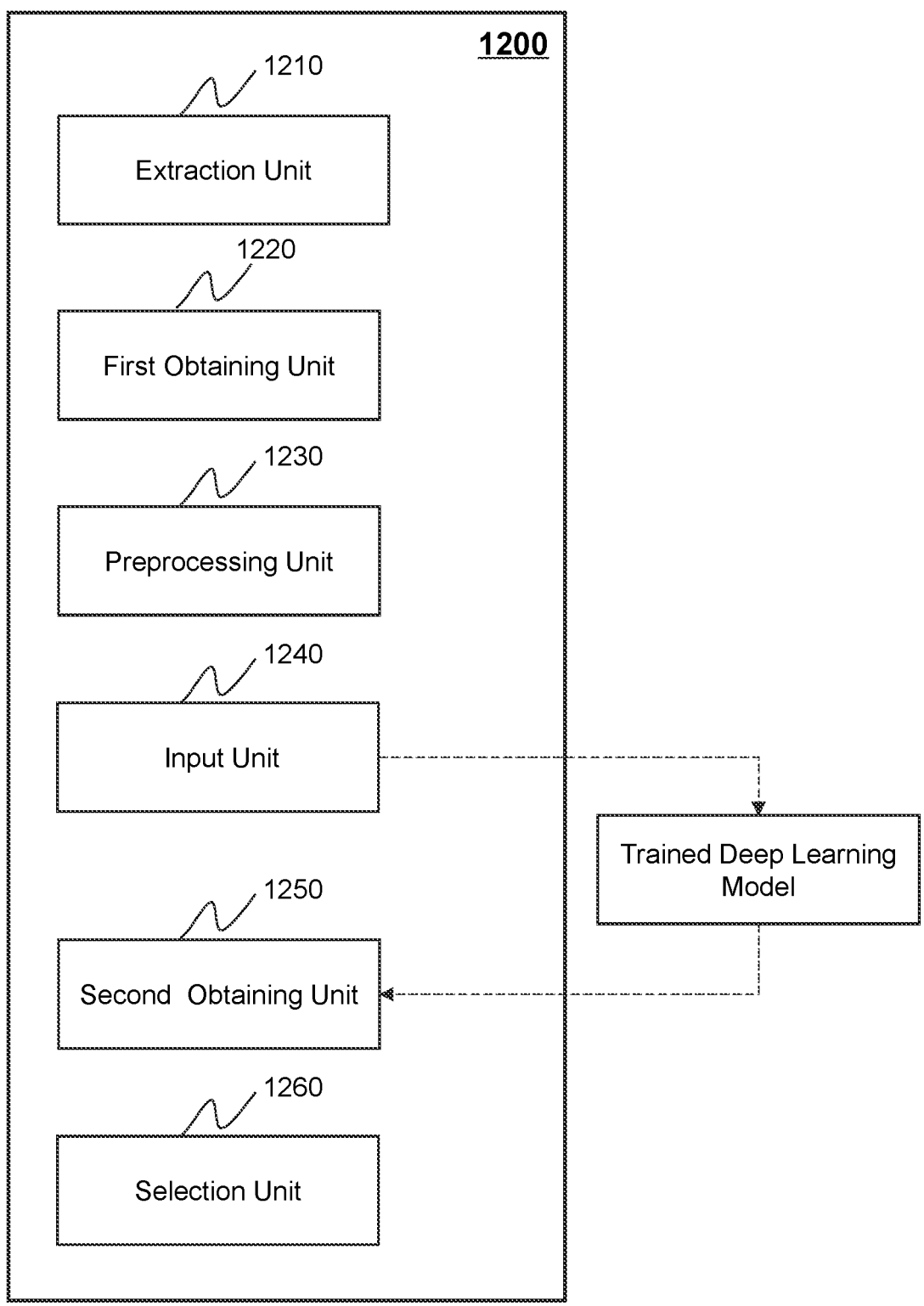
FIG. 12 is a block diagram illustrating an exemplary object recognition device according to some embodiments of the present disclosure.

FIG. 12 is a block diagram illustrating an exemplary object recognition device according to some embodiments of the present disclosure. The object recognition device 1200 may be implemented on the computing device 200 (e.g., the processor 210) illustrated in FIG. 2 or the mobile device 300 illustrated in FIG. 3. The object recognition device 1200 may include an extraction unit 1210, a first obtaining unit 1220, a preprocessing unit 1230, an input unit 1240, a second obtaining unit 1250, and a selection unit 1260.

The extraction unit 1210 may be configured to extract, for each tubular structure in a scanned image, a centerline of the tubular structure. More descriptions regarding the extraction of the centerline of the tubular structure may be found elsewhere in the present disclosure, for example, operation 1110 in FIG. 11 and relevant descriptions thereof.

The first obtaining unit 1220 may be configured to obtain feature parameters of the centerline based on the centerline. More descriptions regarding the obtaining of the feature parameters of the centerline may be found elsewhere in the present disclosure, for example, operation 1120 in FIG. 11 and relevant descriptions thereof.

The preprocessing unit 1230 may be configured to preprocess the feature parameters of the centerline. More descriptions regarding the preprocessing of the feature parameters of the centerline may be found elsewhere in the present disclosure, for example, operation 1130 in FIG. 11 and relevant descriptions thereof.

The input unit 1240 may be configured to input the preprocessed feature parameters of the centerline into a trained deep learning model. In some embodiments, the input unit 1240 may obtain the trained deep learning model from a storage device (e.g., the storage device 150, an external database) or a processing device (e.g., the processing device 120) disclosed elsewhere in the present disclosure. In some embodiments, the object recognition device 1200 may further include a model obtaining unit configured to obtain the trained deep learning model based on a training process. More descriptions regarding the obtaining of the trained deep learning model may be found elsewhere in the present disclosure, for example, FIG. 6 and relevant descriptions thereof. More descriptions regarding the input of the preprocessed feature parameters of the centerline may be found elsewhere in the present disclosure, for example, operation 1140 in FIG. 11 and relevant descriptions thereof.

The second obtaining unit 1250 may be configured to obtain a name of the tubular structure output by the trained deep learning model. More descriptions regarding the obtaining of the name of the tubular structure may be found elsewhere in the present disclosure, for example, operation 1150 in FIG. 11 and relevant descriptions thereof.

The selection unit 1260 may be configured to select a target tubular structure in the scanned image based on the names of the tubular structures in the scanned image. More descriptions regarding the selection of the target tubular structure may be found elsewhere in the present disclosure, for example, operation 1160 in FIG. 11 and relevant descriptions thereof.

The units in the object recognition device 1200 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. In some embodiments, two or more of the units may be combined into a single unit, and any one of the units may be divided into two or more sub-units. In some embodiments, the processing device 120 may include one or more additional units. In some embodiments, one or more of the units may be omitted.

Figure 13:
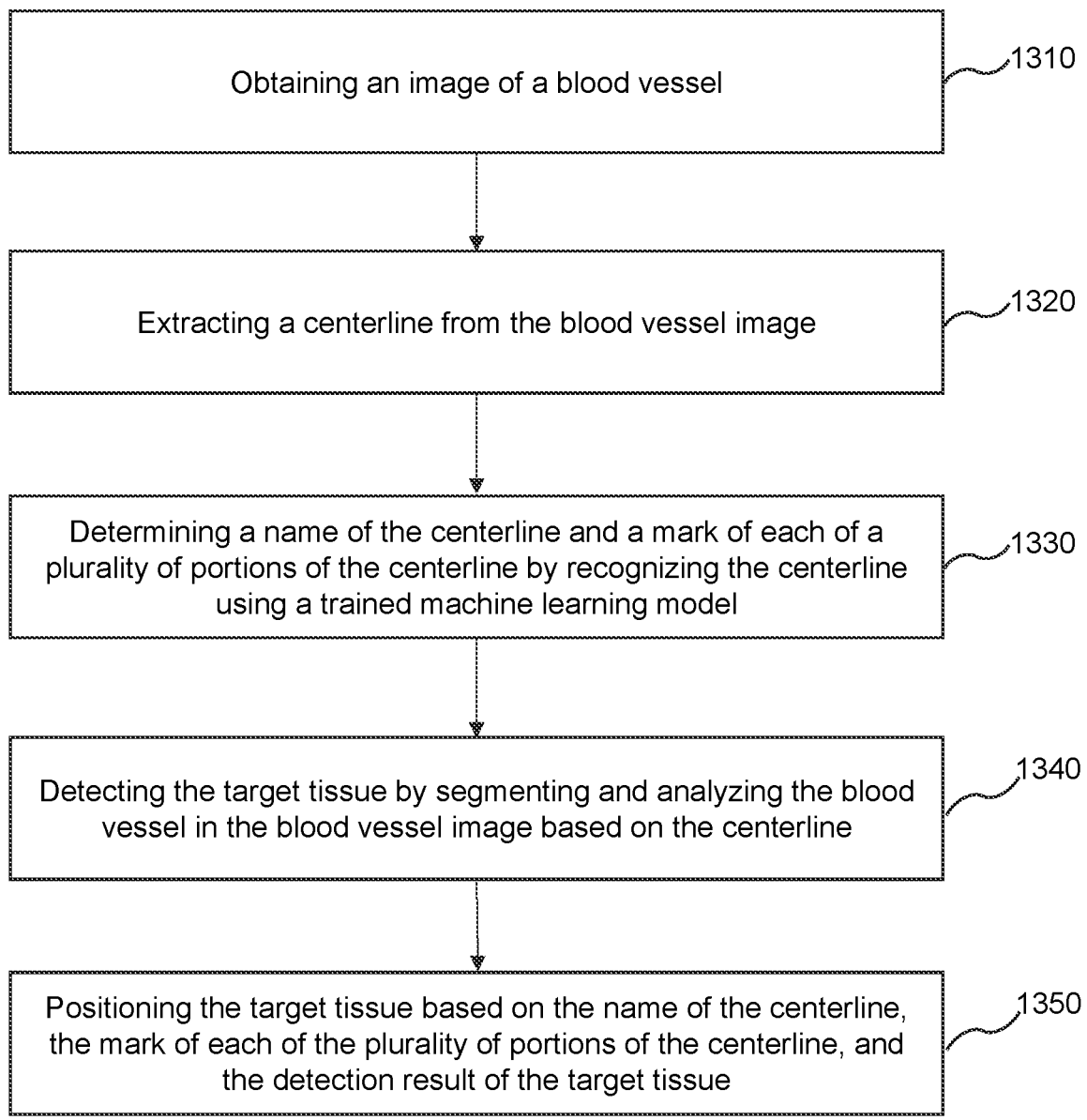
FIG. 13 is a flowchart illustrating an exemplary process for positioning target tissue according to some embodiments of the present disclosure.

FIG. 13 is a flowchart illustrating an exemplary process for positioning target tissue according to some embodiments of the present disclosure. In some embodiments, process 1300 may be executed by the medical system 100. For example, the process 1300 may be implemented as a set of instructions (e.g., an application) stored in a storage device (e.g., the storage device 150, the storage 220, and/or the storage 390). In some embodiments, the processing device 120 (e.g., the processor 210 of the computing device 200, the CPU 340 of the mobile device 300, and/or one or more modules illustrated in FIG. 4) and/or a target tissue positioning device 1700 (e.g., one or more units illustrated in FIG. 17) illustrated in FIG. 17 may execute the set of instructions and may accordingly be directed to perform the process 1300. The operations of the illustrated process presented below are intended to be illustrative. In some embodiments, the process 1300 may be accomplished with one or more additional operations not described and/or without one or more of the operations discussed. Additionally, the order of the operations of process 1300 illustrated in FIG. 13 and described below is not intended to be limiting.

In 1310, an image of a blood vessel (also referred to as a blood vessel image) may be obtained. The blood vessel may be an example of the tubular structure disclosed elsewhere in the present disclosure. The blood vessel image may be an example of the scanned image disclosed elsewhere in the present disclosure. In some embodiments, operation 1310 may be performed by the processing device 120 (e.g., the obtaining module 410 illustrated in FIG. 4) (e.g., the interface circuits of the processor 220) and/or the target tissue positioning device 1700 (e.g., an image obtaining unit 1710 illustrated in FIG. 17).

In some embodiments, the blood vessel image may be obtained from a database communicated with or integrated into the medical system 100. Additionally or alternatively, the blood vessel image may be obtained by an imaging device (e.g., the imaging device 110).

In some embodiments, the blood vessel image may be acquired by an imaging device (e.g., an MR device) according to one single sequence (also referred to as a pulse sequence) or a plurality of sequences. The sequence may include a bright blood sequence and/or a black blood sequence. The bright blood sequence may include a time of flight (Tof) sequence. An image acquired based on the black blood sequence may include a T1 enhanced image, a T1 image, a T2 image, a proton density image, etc. In some embodiments, the blood vessel image may include a single image layer (also referred to as an image slice) acquired based on the single sequence or a plurality of image layers of the same position or portion of the blood vessel acquired based on a plurality of registration sequences. Since scanning protocols of different imaging devices are different, the blood vessel image acquired based on different scanning protocols of the imaging devices may be different. The blood vessel image may include one single image layer acquired by an imaging device according to the single sequence, the plurality of image layers of the same position or portion of the blood vessel acquired based on a plurality of registration sequences, or one of the plurality of image layers.

In 1320, a centerline may be extracted from the blood vessel image. In some embodiments, operation 1320 may be performed by the processing device 120 (e.g., the centerline determination module 420 illustrated in FIG. 4) (e.g., the processing circuits of the processor 220) and/or the target tissue positioning device 1700 (e.g., a centerline extraction unit 1720 illustrated in FIG. 17).

In some embodiments, the centerline may be extracted from the blood vessel image using a registration algorithm. Specifically, a registration relationship between the blood vessel image and an image including a known blood vessel centerline may be determined by registering the blood vessel image with the image including the known blood vessel centerline. According to the registration relationship, the centerline in the blood vessel image may be obtained.

In some embodiments, the centerline may be extracted from the blood vessel image using an interactive detection algorithm. Specifically, at least two positioning points on the blood vessel represented in the blood vessel image may be obtained. An optimal route between the at least two positioning points may be determined. According to the optimal route, the centerline in the blood vessel image may be obtained.

In some embodiments, the centerline may be extracted from the blood vessel image using an automatic detection algorithm. For example, the centerline may be extracted from the blood vessel image using a trained neural network model. The extraction of the centerline using the trained neural network model may be performed in a similar manner as process 1100, and relevant descriptions are not repeated here. As another example, the centerline may be extracted from the blood vessel image using a traditional machine learning algorithm, such as a template matching algorithm.

In 1330, a name of the centerline and a mark of each of a plurality of portions of the centerline may be determined by recognizing the centerline using a trained machine learning model. In some embodiments, operation 1330 may be performed by the processing device 120 (e.g., the recognition module 430 illustrated in FIG. 4) (e.g., the processing circuits of the processor 220) and/or the target tissue positioning device 1700 (e.g., a centerline naming and marking unit 1730 illustrated in FIG. 17).

In some embodiments, the trained machine learning model may be provided by a processing device that is the same as or different from the processing device 120 online or offline. For example, the processing device may obtain a plurality of training samples. The plurality of training samples may include a plurality of training images (e.g., blood vessel images). Each of the plurality of training images may include one or more centerlines extracted from the training image, names of the one or more centerlines, and a mark of each of a plurality of portions of each centerline. The trained machine learning model may be obtained by iteratively training a preliminary machine learning model based on the plurality of training samples. The trained machine learning model obtained based on the plurality of training samples may have high identification efficiency and high accuracy. The trained machine learning model may include the trained neural network model disclosed elsewhere in the present disclosure. The trained neural network model may include but is not limited to a convolutional neural network (CNN) model, a deep belief network (DBN) model, a recurrent neural network (RNN) model, a recurrent neural tensor network (RNTN) model, etc.

When the blood vessel image includes the plurality of image layers of the same position or portion of the blood vessel acquired based on the plurality of registration sequences, for each of the plurality of image layers, a centerline may be extracted from the image layer. A name of the centerline and a mark of each of a plurality of portions of the centerline may be determined. For each of the plurality of portions of the centerline, a mark of the portion of the centerline may include a name and/or a label of the portion of the centerline. For example, for the vertebral artery in cerebral vessels, marks of portions of the vertebral artery may include the outer bone segment (i.e., V1 segment; the intervertebral foramina segment (i.e., V2 segment); the outer spinal segment (i.e., V3 segment); the intradural segment (i.e., V4 segment). The V1 segment may be a label of a portion of the vertebral artery named as the outer bone segment. The V2 segment may be a label of a portion of the vertebral artery named as the intervertebral foramina segment. The V3 segment may be a label of a portion of the vertebral artery named as the outer spinal segment. The V4 segment may be a label of a portion of the vertebral artery named as the intradural segment. As another example, for the internal carotid artery, marks of portions of the internal carotid artery may include the strong segment (i.e., C1 segment); the rock segment (i.e., C2 segment); the fractured hole segment (i.e., C3 segment); the cavernous sinus segment (i.e., C4 segment); the bed protrusion segment (i.e., C5 segment); the eye segment (i.e., C6 segment); and the traffic segment (i.e., C7 segment).

In some embodiments, marks of the plurality of portions of the centerline may be determined by adding labels to an endpoint of each portion of the centerline (e.g., a blood vessel). A position (e.g., coordinates) of each portion of the centerline may be determined based on other images of the centerline. Further, the mark of each of the plurality of portions of the centerline may be saved as a segmented text file. The segmented text file corresponding to a portion of the centerline may include the label of the portion of the centerline, coordinates of the label, the name of the portion of the centerline.

In 1340, target tissue may be detected by segmenting and analyzing the blood vessel in the blood vessel image based on the centerline. In some embodiments, operation 1340 may be performed by the processing device 120 (e.g., the abnormality determination module 430 illustrated in FIG. 4) (e.g., the processing circuits of the processor 220) and/or the target tissue positioning device 1700 (e.g., a target tissue detection unit 1740 illustrated in FIG. 17).

In some embodiments, the target tissue may refer to tissue including an abnormality (e.g., a lesion). A positioning report may be generated based on information associated with the abnormality obtained during analyzing the blood vessel. The positioning report may include a name of the target tissue, a position of the target tissue, and a mark of a portion of the centerline including the target tissue. The position (e.g., a blood vessel or a portion of the blood vessel where the target tissue is located) of the target tissue may be quickly determined, thereby facilitating subsequent pathological analysis. More descriptions regarding the detection of the target tissue may be found elsewhere in the present disclosure. See, e.g., FIG. 14 and the description thereof.

In 1350, the target tissue may be positioned based on the name of the centerline, the mark of each of the plurality of portions of the centerline, and the detection result of the target tissue. In some embodiments, operation 1350 may be performed by the processing device 120 (e.g., the abnormality determination module 430 illustrated in FIG. 4) (e.g., the processing circuits of the processor 220) and/or the target tissue positioning device 1700 (e.g., a target tissue positioning unit 1750 illustrated in FIG. 17).

In the present disclosure, the centerline may be extracted from the blood vessel image. The name of the centerline and the mark of each of the plurality of portions of the centerline may be determined by recognizing the centerline using the trained machine learning model. The target tissue may be detected by segmenting and analyzing the blood vessel in the blood vessel image based on the centerline. Further, the target tissue may be positioned based on the name of the centerline, the mark of each of the plurality of portions of the centerline, and the detection result of the target tissue. The above process may be performed without manual participation, thereby avoiding the influence of human factors. Moreover, the use of the trained machine learning model may improve the efficiency of the name of the centerline and the mark of each of the plurality of portions of the centerline, thereby realizing the rapid and accurate positioning of the target tissue based on the name of the centerline, the mark of each of the plurality of portions of the centerline, and the detection result.

It should be noted that the above description regarding the process 1300 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted.

Figure 14:
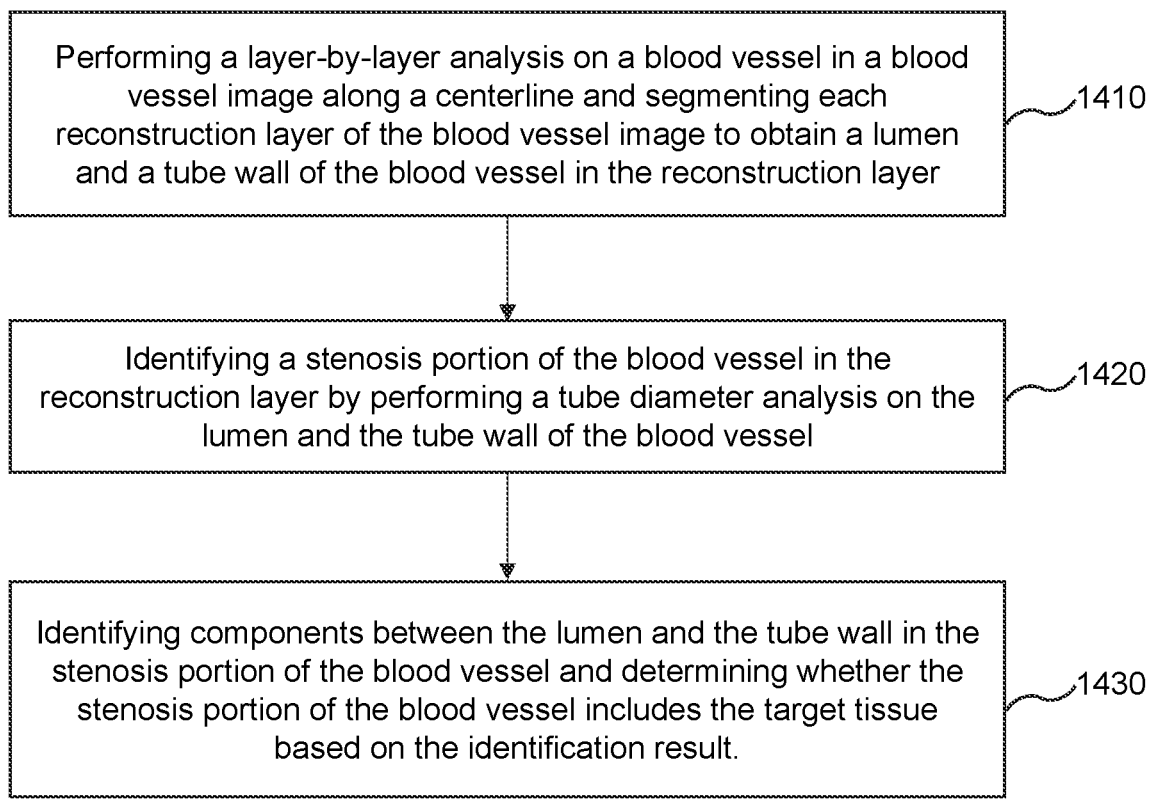
FIG. 14 is a flowchart illustrating an exemplary process for detecting target tissue according to some embodiments of the present disclosure.

FIG. 14 is a flowchart illustrating an exemplary process for detecting target tissue according to some embodiments of the present disclosure. In some embodiments, process 1400 may be executed by the medical system 100. For example, the process 1400 may be implemented as a set of instructions (e.g., an application) stored in a storage device (e.g., the storage device 150, the storage 220, and/or the storage 390). In some embodiments, the processing device 120 (e.g., the processor 210 of the computing device 200, the CPU 340 of the mobile device 300, and/or one or more modules illustrated in FIG. 4) and/or the target tissue positioning device 1700 (e.g., one or more units illustrated in FIG. 17) illustrated in FIG. 17 may execute the set of instructions and may accordingly be directed to perform the process 1400. The operations of the illustrated process presented below are intended to be illustrative. In some embodiments, the process 1400 may be accomplished with one or more additional operations not described and/or without one or more of the operations discussed. Additionally, the order of the operations of process 1400 illustrated in FIG. 14 and described below is not intended to be limiting.

In 1410, a blood vessel in a blood vessel image may be analyzed along a centerline recognized from the blood vessel image. Further, each reconstruction layer (also referred to as a reconstruction image of a layer) of the blood vessel image may be segmented to obtain a lumen and a tube wall of the blood vessel in the reconstruction layer. In some embodiments, operation 1410 may be performed by the processing device 120 (e.g., the abnormality determination module 430 illustrated in FIG. 4) (e.g., the processing circuits of the processor 220) and/or the target tissue positioning device 1700 (e.g., the target tissue detection unit 1740 illustrated in FIG. 17).

Figure 15:
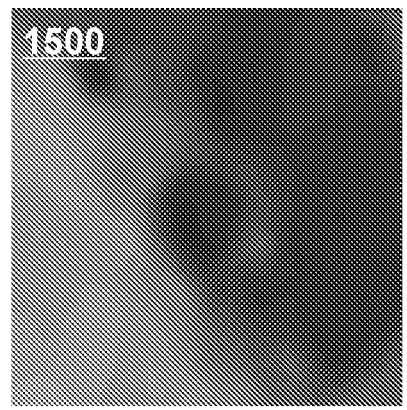
FIG. 15 is a schematic diagram illustrating an exemplary reconstruction layer of a blood vessel image according to some embodiments of the present disclosure.
Figure 16:
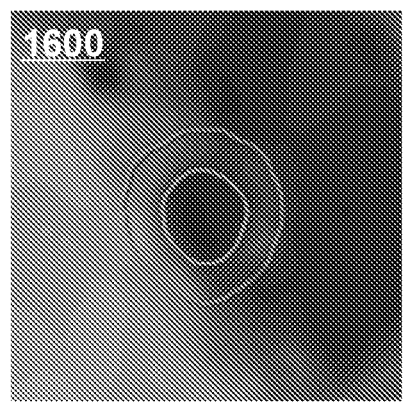
FIG. 16 is a schematic diagram illustrating an exemplary segmented image obtained by segmenting the reconstruction layer illustrated in FIG. 15 according to some embodiments of the present disclosure.

The analysis of the blood vessel in the blood vessel image along the centerline may refer to analyzing the blood vessel based on image slices or layers each of which represents a layer of the blood vessel with a certain thickness in a direction perpendicular to the centerline. In some embodiments, when the blood vessel image is acquired by an imaging device (e.g., an MR device) according to a signal sequence, for each layer with a certain thickness of the blood vessel in a direction perpendicular to the centerline of the blood vessel, a reconstruction image (i.e., an image slice or layer) representing the layer of the blood vessel may be obtained. As shown in FIG. 15, an image 1500 may be a reconstruction image of a certain layer of the blood vessel in a direction perpendicular to the centerline of the blood vessel. When the blood vessel image is acquired by an imaging device (e.g., an MR device) according to a plurality of sequences, the blood vessel image may include multiple images each of which is acquired based on one of the plurality of sequences. For each of the multiple images corresponding to one of the plurality of sequences, a reconstruction image (i.e., an image slice or layer) representing the layer of the blood vessel may be obtained. The reconstruction image may refer to an image slice obtained at a certain point on the centerline along a direction perpendicular to the centerline according to a certain size and using a certain interpolation manner. In some embodiments, the reconstruction image may be obtained using a bicubic interpolation manner. Further, the reconstruction image may be segmented based on an image processing manner to obtain the lumen and the tube wall of the blood vessel in each reconstruction image along the centerline. As shown in FIG. 16, an image 1600 may be the segmented image obtained by segmenting the reconstruction image 1500 illustrated in FIG. 15.

In 1420, a stenosis portion of the blood vessel in the reconstruction image may be identified by performing a tube diameter analysis on the lumen and the tube wall of the blood vessel. In some embodiments, operation 1420 may be performed by the processing device 120 (e.g., the abnormality determination module 430 illustrated in FIG. 4) (e.g., the processing circuits of the processor 220) and/or the target tissue positioning device 1700 (e.g., the target tissue detection unit 1740 illustrated in FIG. 17).

In some embodiments, at least one quantitative parameter (e.g., the structural parameter, the component parameter) of the lumen and the tube wall may be determined. The at least one quantitative parameter may include an area of the lumen, an area of the tube wall, a thickness of the tube wall, or the like, or any combination thereof. The at least one quantitative parameter of the lumen and the tube wall may be determined using an image processing manner. According to the at least one quantitative parameter of the lumen and the tube wall, the stenosis portion of the blood vessel may be identified. Specifically, the stenosis portion of the blood vessel may be identified based on the area of the lumen, the area of the tube wall, and/or the thickness of the tube wall. Merely by way of example, the stenosis portion of the blood vessel may be identified by comparing a quantitative parameter of the lumen of the tube wall with a standard reference parameter. For example, if the standard reference parameter of an area of the tube wall is 72 and the area of the tube wall in the determined quantitative parameter is 13, the portion of the blood vessel corresponding to the tube wall may be identified as the stenosis portion of the blood vessel. The tube diameter analysis may refer to a process of determining the at least one quantitative parameter of the lumen and the tube wall and identifying the stenosis portion of the blood vessel.

In 1430, components between the lumen and the tube wall in the stenosis portion of the blood vessel may be identified. Further, whether the stenosis portion of the blood vessel includes the target tissue (e.g., an abnormality) may be determined based on the identification result. In some embodiments, operation 1430 may be performed by the processing device 120 (e.g., the abnormality determination module 430 illustrated in FIG. 4) (e.g., the processing circuits of the processor 220) and/or the target tissue positioning device 1700 (e.g., the target tissue detection unit 1740 illustrated in FIG. 17).

In some embodiments, after the stenosis portion of the blood vessel in the reconstruction images is identified, the components between the lumen and the tube wall in the stenosis portion may be identified and marked. The components may include a calcification, a lipid core, a loose matrix, a fiber cap, or the like, or any combination thereof. Merely by way of example, the components may be identified and marked using an image processing technique. Further, an area and/or a proportion of each component may be quantitatively calculated. According to the calculation result, whether the stenosis portion of the blood vessel includes the target tissue may be determined. Merely by way of example, when an area or a proportion of a component in the calculation result reaches a certain threshold, the stenosis portion of the blood vessel may include the target tissue. In the present disclosure, the calculation of the area and/or the proportion of each component may be used to quickly determine the position (e.g., a blood vessel or a portion of the blood vessel where the target tissue is located) of the target tissue, thereby facilitating subsequent pathological analysis.

It should be noted that the above description regarding the process 1400 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted.

Figure 17:
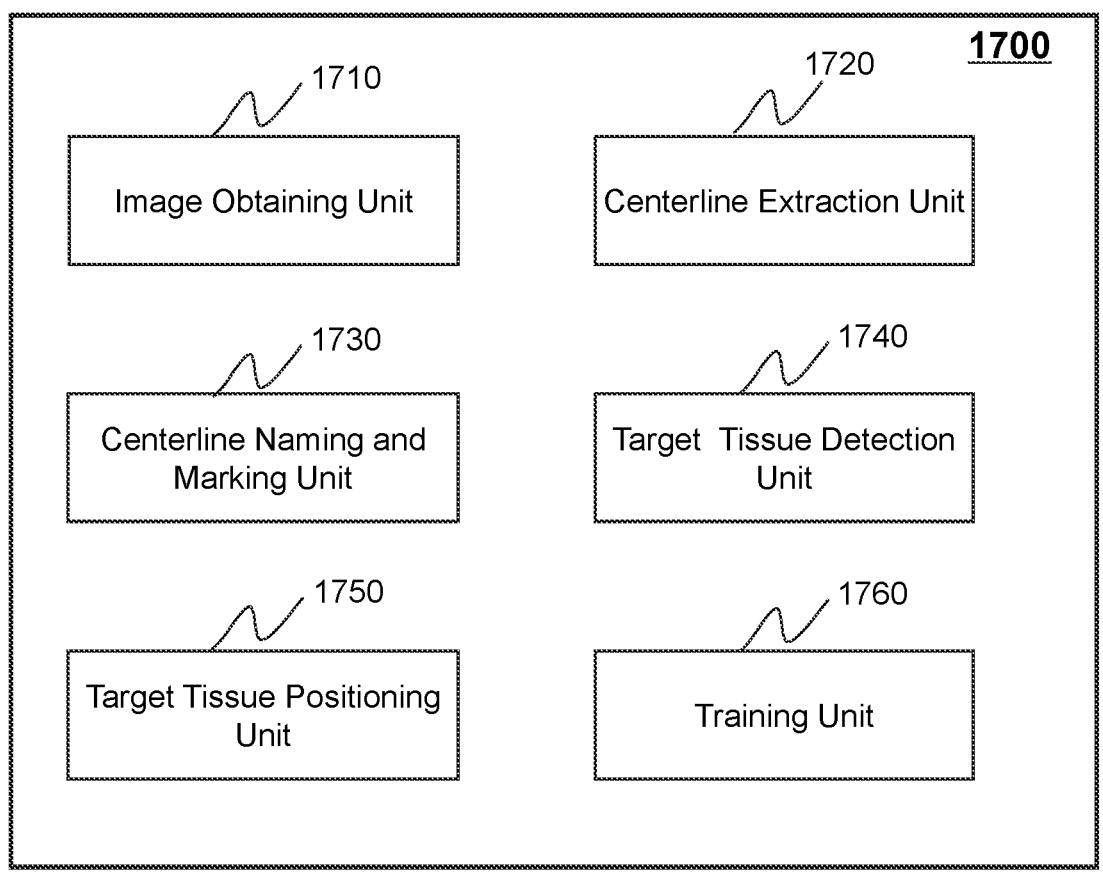
FIG. 17 is a block diagram illustrating an exemplary target tissue positioning device according to some embodiments of the present disclosure.

FIG. 17 is a block diagram illustrating an exemplary target tissue positioning device according to some embodiments of the present disclosure. The target tissue positioning device 1700 may be implemented on the computing device 200 (e.g., the processor 210) illustrated in FIG. 2 or the mobile device 300 illustrated in FIG. 3. The target tissue positioning device 1700 may include an image obtaining unit 1710, a centerline extraction unit 1720, a centerline naming and marking unit 1730, a target tissue detection unit 1740, a target tissue positioning unit 1750, and a training unit 1760.

The image obtaining unit 1710 may be configured to obtain an image of a blood vessel. More descriptions regarding the obtaining of the image of the blood vessel may be found elsewhere in the present disclosure, for example, operation 1310 in FIG. 13 and relevant descriptions thereof.

The centerline extraction unit 1720 may be configured to extract a centerline from the blood vessel image. More descriptions regarding the extraction of the centerline may be found elsewhere in the present disclosure, for example, operation 1320 in FIG. 13 and relevant descriptions thereof.

The centerline naming and marking unit 1730 may be configured to determine a name of the centerline and a mark of each of a plurality of portions of the centerline by recognizing the centerline using a trained machine learning model. More descriptions regarding the determination of the name of the centerline and the mark of each of the plurality of portions of the centerline may be found elsewhere in the present disclosure, for example, operation 1330 in FIG. 13 and relevant descriptions thereof.

The target tissue detection unit 1740 may be configured to detect target tissue by segmenting and analyzing the blood vessel in the blood vessel image based on the centerline. In some embodiments, the target tissue detection unit 1740 may include a first analysis sub-unit, a second analysis sub-unit, and an identification sub-unit. The first analysis sub-unit may be configured to analyze a blood vessel in a blood vessel image along a centerline recognized from the blood vessel image. The second analysis sub-unit may be configured to identify a stenosis portion of the blood vessel in the reconstruction image by performing a tube diameter analysis on the lumen and the tube wall of the blood vessel. The identification sub-unit may be configured to identify components between the lumen and the tube wall in the stenosis portion of the blood vessel. More descriptions regarding the detection of the target tissue may be found elsewhere in the present disclosure, for example, operation 1340 in FIG. 13, FIG. 14, and relevant descriptions thereof.

The target tissue positioning unit 1750 may be configured to position the target tissue based on the name of the centerline, the mark of each of the plurality of portions of the centerline, and the detection result of the target tissue. More descriptions regarding the positioning of the target tissue may be found elsewhere in the present disclosure, for example, operation 1350 in FIG. 13 and relevant descriptions thereof.

The training unit 1760 may be configured to obtain the trained machine learning model based on a training process. More descriptions regarding the obtaining of the trained machine learning model may be found elsewhere in the present disclosure, for example, FIG. 6 and relevant descriptions thereof.

The units in the target tissue positioning device 1700 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. In some embodiments, two or more of the units may be combined into a single unit, and any one of the units may be divided into two or more sub-units. In some embodiments, the processing device 120 may include one or more additional units. In some embodiments, one or more of the units may be omitted. For example, the training unit 1760 may be omitted.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or component of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction performing system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
   at least one storage device including a set of instructions; and
   at least one processor in communication with the at least one storage device, wherein when executing the set of instructions, the at least one processor is directed to perform operations including:
      obtaining image data captured by an imaging device, the image data including one or more objects;
      determining a centerline of a target object in the one or more objects based on the image data, the target object including a tubular structure; and
      determining a recognition result of the target object based on an output of a trained neural network model that takes at least one feature parameter of the centerline of the target object as input, the recognition result including at least one of a name of the target object or a label of the target object.

2. The system of claim 1, wherein the determining a recognition result of the target object includes:
   determining, based on the image data, a reference centerline of at least one reference object associated with the target object among the one or more objects, the centerline of the target object and the reference centerline of the at least one reference object forming a centerline tree;
   determining at least one feature parameter of the centerline tree; and
   determining the recognition result of the target object based on an output of the trained neural network model that takes the at least one feature parameter of the centerline of the target object and the at least one feature parameter of the centerline tree as input.

3. The system of claim 2, wherein the at least one feature parameter of the centerline of the target object includes at least one of position information of the centerline in the image data, position information of the centerline in the centerline tree, information of the centerline tree, or size information of the centerline.

4. The system of claim 2, wherein the trained neural network model includes:
   a first recognition module configured to determine, based on the at least one feature parameter of the centerline, a preliminary recognition result of the target object;
   an extraction module configured to determine, based on the centerline tree, the at least one feature parameter of the centerline tree; and
   a second recognition module configured to determine the recognition result of the target object based on the preliminary recognition result and the at least one feature parameter of the centerline tree.

5. The system of claim 4, wherein:
   the target object includes a plurality of portions,
   to determine, based on the at least one feature parameter of the centerline, a preliminary recognition result of the target object, the first recognition module is further configured to:
      determine the preliminary recognition result of the target object based on at least one feature parameter of a portion of the centerline corresponding to each of at least one of the plurality of portions in the target object.

6. The system of claim 4, wherein:
   the extraction module includes a recurrent neural network model, the recurrent neural network model including a plurality of nodes, and
   to determine, based on the centerline tree, the at least one feature parameter of the centerline tree, the extraction module is further configured to:
      determine the at least one feature parameter of the centerline tree by inputting at least one feature parameter of each centerline in the centerline tree into one of the plurality of nodes corresponding to the centerline in the centerline tree.

7. The system of claim 1, wherein the trained neural network model is obtained by a training process including:
   obtaining a plurality of training samples associated with a plurality of sample objects, each of the plurality of training samples including at least one feature parameter of a centerline of a sample object associated with the training sample and at least one of a name of the sample object or a label of the sample object; and
   obtaining the trained neural network model by iteratively training a preliminary neural network model based on the plurality of training samples, wherein:
   in each iteration,
      at least one feature parameter of a centerline of a sample object is used as an input of the preliminary neural network model, the at least one of the name of the sample object or the label of the sample object is used as a reference output of the preliminary neural network model, values of model parameters of the preliminary neural network model are updated by comparing the reference output and an estimated output of the preliminary neural network model generated based on the input of the preliminary neural network model.

8. The system of claim 7, wherein the trained neural network model includes a recurrent neural network (RNN) or a long short-term memory (LSTM) neural network.

9. The system of claim 7, wherein:
each of the plurality of training samples includes at least one feature parameter of a centerline tree corresponding to a sample object associated with the training sample,
the obtaining a plurality of training samples associated with a plurality of sample objects includes:
extracting a centerline of each sample object in a sample image;
labeling the centerline of the sample object as an anatomical name of the sample object; and
determining a centerline tree associated with the sample object based on the centerline of the sample object, the centerline tree associated with the sample object including the centerline of the sample object and a reference centerline of at least one reference object associated with the sample object.

10. The system of claim 1, wherein the target object includes a plurality of portions, the recognition result of the target object includes at least one of a name or a label of each of the plurality of portions.

11. The system of claim 1, wherein the at least one processor is directed to perform operations further including:
determining whether the target object includes an abnormality; and
in response to determining that the target object includes the abnormality, determining location information of the abnormality based on the recognition result of the target object.

12. The system of claim 11, wherein the determining whether the target object includes an abnormality includes:
obtaining a plurality of image slices of the target object, each of the plurality of image slices representing a layer of the target object in a direction perpendicular to the centerline of the target object;
for each of the plurality of image slices,
obtaining at least one feature parameter of the target object from the image slice; and
determining whether the target object includes the abnormality based on the at least one feature parameter of the target object obtained from the image slice.

13. The system of claim 12, wherein:
the at least one feature parameter of the target object includes at least one structural parameter of a lumen or a tube wall of the tubular structure,
the determining whether the target object includes the abnormality based on the at least one feature parameter of the target object obtained from the image slice includes:
performing a tube diameter analysis on the tubular structure based on the at least one structural parameter of the lumen or the tube wall of the tubular structure; and determining whether the target object includes the abnormality based on the tube diameter analysis result.

14. The system of claim 1, wherein the image data includes a plurality of image slices representing a same position of the subject, each of the plurality of image slices being acquired by the imaging device according to one of a plurality of registration sequences.

15. A method implemented on a computing device including at least one processor, at least one storage medium, and a communication platform connected to a network, the method comprising:
obtaining image data captured by an imaging device, the image data including one or more objects;
determining a centerline of a target object in the one or more objects based on the image data, the target object including a tubular structure; and
determining a recognition result of the target object based on an output of a trained neural network model that takes at least one feature parameter of the centerline of the target object as input, the recognition result including at least one of a name of the target object or a label of the target object.

16. The method of claim 15, wherein the determining a recognition result of the target object includes:
determining, based on the image data, a reference centerline of at least one reference object associated with the target object among the one or more objects, the centerline of the target object and the reference centerline of the at least one reference object forming a centerline tree;
determining at least one feature parameter of the centerline tree; and
determining the recognition result of the target object based on an output of the trained neural network model that takes the at least one feature parameter of the centerline of the target object and the at least one feature parameter of the centerline tree as input.

17. The method of claim 16, wherein the trained neural network model includes:
a first recognition module configured to determine, based on the at least one feature parameter of the centerline, a preliminary recognition result of the target object;
an extraction module configured to determine, based on the centerline tree, the at least one feature parameter of the centerline tree; and
a second recognition module configured to determine the recognition result of the target object based on the preliminary recognition result and the at least one feature parameter of the centerline tree.

18. The method of claim 15, the method further including:
determining whether the target object includes an abnormality; and
in response to determining that the target object includes the abnormality, determining location information of the abnormality based on the recognition result of the target object.

19. A non-transitory computer readable medium, comprising executable instructions that, when executed by at least one processor, direct the at least one processor to perform a method, the method comprising:
obtaining image data captured by an imaging device, the image data including one or more objects;
determining a centerline of a target object in the one or more objects based on the image data, the target object including a tubular structure; and determining a recognition result of the target object based on an output of a trained neural network model that takes at least one feature parameter of the centerline of the target object as input, the recognition result including at least one of a name of the target object or a label of the target object.

* * * * *